US010561767B2

(12) United States Patent
Thompson et al.

(10) Patent No.: US 10,561,767 B2
(45) Date of Patent: Feb. 18, 2020

(54) MEDICAL SUCTION DEVICE

(71) Applicant: UMPQUA RESEARCH COMPANY, Myrtle Creek, OR (US)

(72) Inventors: John O. Thompson, Myrtle Creek, OR (US); William F. Michalek, Roseburg, OR (US); John T. Holtsnider, Riddle, OR (US)

(73) Assignee: UMPQUA RESEARCH COMPANY, Myrtle Creek, OR (US)

( * ) Notice: Subject to any disclaimer, the term of this patent is extended or adjusted under 35 U.S.C. 154(b) by 671 days.

(21) Appl. No.: 15/294,521

(22) Filed: Oct. 14, 2016

(65) Prior Publication Data

US 2017/0112977 A1    Apr. 27, 2017

Related U.S. Application Data

(60) Provisional application No. 62/244,629, filed on Oct. 21, 2015.

(51) Int. Cl.
| *A61M 1/00* | (2006.01) |
| *A61M 13/00* | (2006.01) |
| *A61M 27/00* | (2006.01) |
| *A61F 13/00* | (2006.01) |
| *A61B 17/50* | (2006.01) |

(52) U.S. Cl.
CPC ........ *A61M 1/0056* (2013.01); *A61M 1/0017* (2014.02)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS

| 4,930,997 A | 6/1990 | Bennett |
| 5,037,457 A * | 8/1991 | Goldsmith ............. B01D 69/10 |
| | | 156/162 |

(Continued)

FOREIGN PATENT DOCUMENTS

EP    2968702 A2 *    1/2016

OTHER PUBLICATIONS

Llyod, C. "Medical Evaluations on the KC-135 1991 Flight Report Summary," NASA Technical Memorandum 104755, Aug. 1993, 260 pages.

(Continued)

*Primary Examiner* — Tatyana Zalukaeva
*Assistant Examiner* — Ilya Y Treyger
(74) *Attorney, Agent, or Firm* — McCoy Russell LLP

(57) ABSTRACT

Systems and methods for a cartridge which may be included in a medical suction device are disclosed herein. In one embodiment, a cartridge may comprise a porous filler material loaded with absorption granules for absorbing liquids, and a hydrophobic liquid barrier which is permeable only to one or more of air and gasses, and positioned within the cartridge so that liquids in the cartridge cannot exit the cartridge. The cartridge may further comprise perforated walls and sealed walls, arranged within the cartridge in an alternating order and orientated parallel to one another and perpendicular to a net flow direction of fluids in the cartridge, and spaced from one another such that passages are formed between the walls.

18 Claims, 8 Drawing Sheets

(56) References Cited

U.S. PATENT DOCUMENTS 5,779,674 A * 7/1998 Ford ............... A61M 5/38
604/122
2007/0084866 A1* 4/2007 Saeugling ............. B65D 31/02
220/495.06

OTHER PUBLICATIONS

Furgiuele, C. et al., "Evolution of In-Flight Medical Care from Space Shuttle to International Space Station," 26th International Conference on Environmental Systems, Jul. 8, 1996, Monterey, California, 10 pages.
Liu, M. et al., "Preparations and Swelling Properties of Crosslinked Sodium Polyacrylate," Journal of Applied Polymer Science, vol. 82, No. 6, Nov. 7, 2001, Published Online Aug. 29, 2001, 6 pages.
Williams, D., "The Biomedical Challenges of Space Flight," Annual Review of Medicine, vol. 54, Feb. 2003, Published Online Nov. 21, 2002, 15 pages.
Dai, Q. et al., "Preparation and Proeperties of Polydimethylsiloxane/Polyacrylate Composite Latex Initiated by 60Co γ-Ray Irradiation," Journal of Applied Polymer Science, vol. 88, No. 12, Jun. 20, 2003, Published Online Mar. 26, 2003, 5 pages.
Ma, S. et al., "Preparation and Properties of a Salt-Resistant Superabsorbent Polymer," Journal of Applied Polymer Science, vol. 93, No. 6, Sep. 15, 2004, Published Online Jul. 7, 2004, 10 pages.
Watkins, S. et al., "The Space Medicine Exploration Medical Condition List" The University of Texas Medical Branch, NASA/Johnson Space Center Bioastronautics Contract, Mar. 2010, 1 page.

* cited by examiner

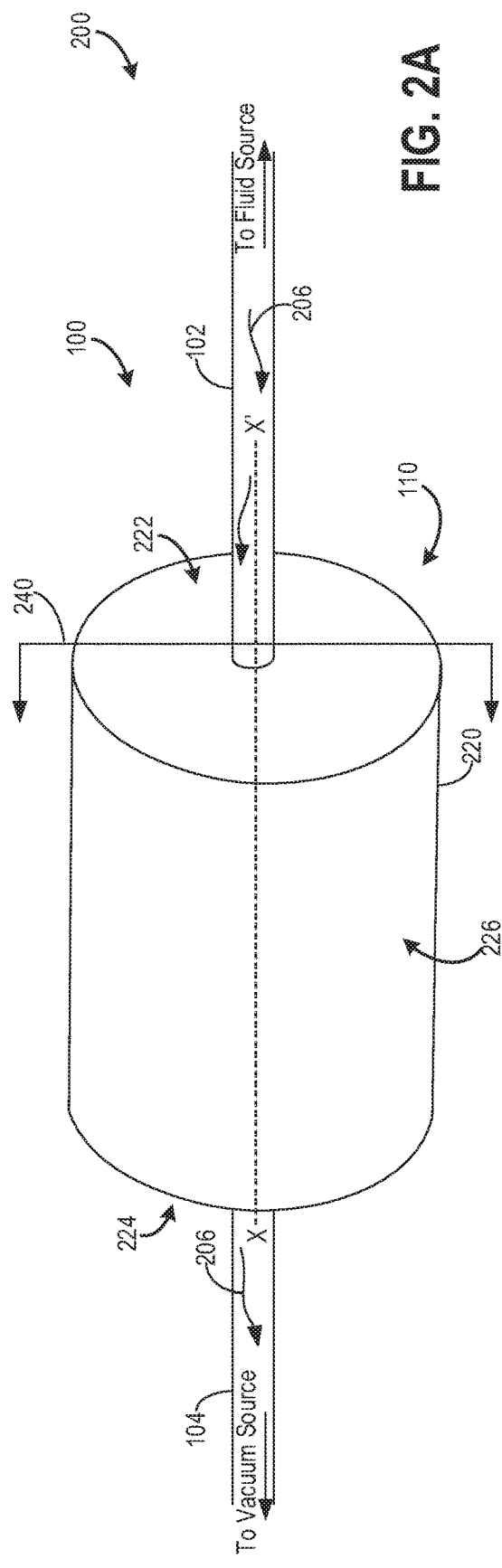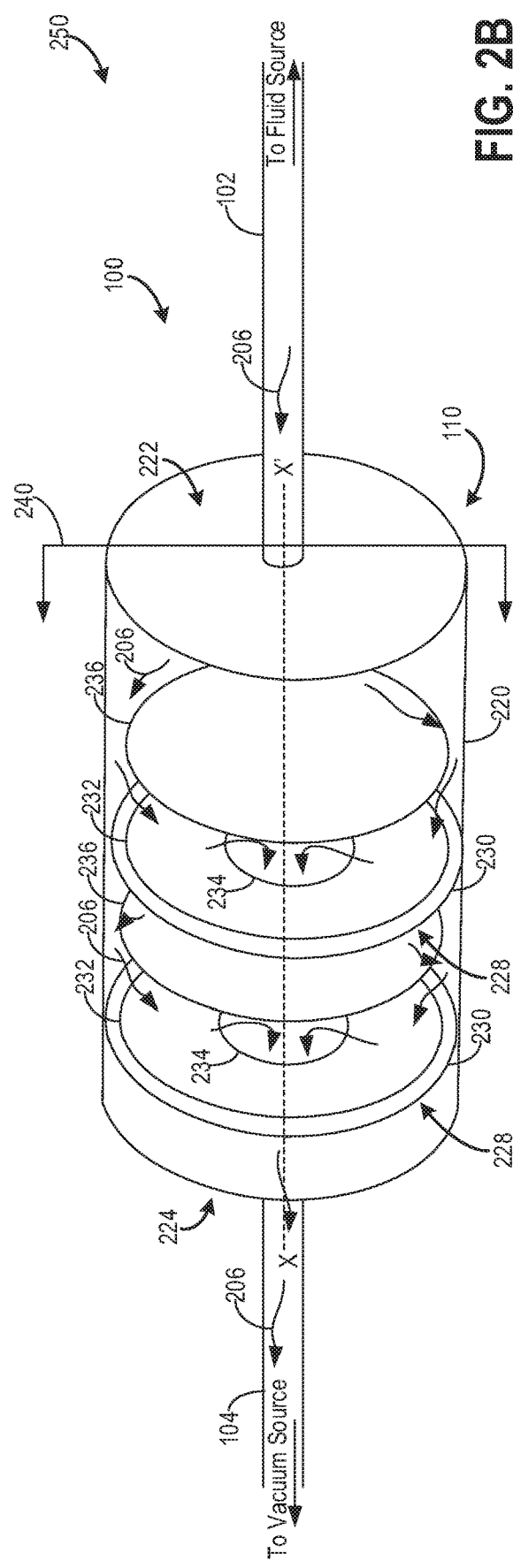

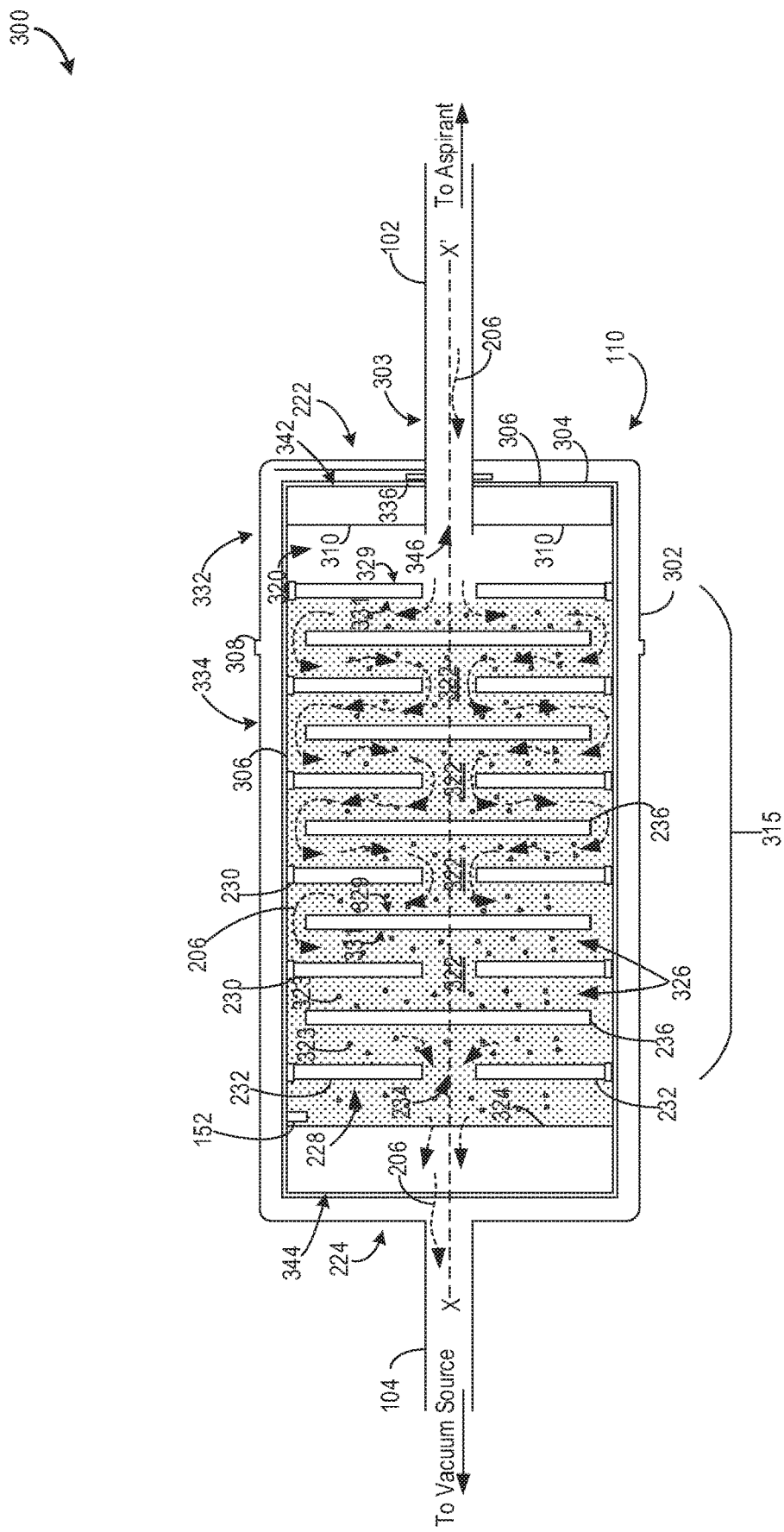

MEDICAL SUCTION DEVICE

CROSS REFERENCE TO RELATED APPLICATIONS

The present application claims priority to U.S. Provisional Patent Application No. 62/244,629, entitled "MEDICAL SUCTION DEVICE," and filed on Oct. 21, 2015, the entire contents of which are hereby incorporated by reference for all purposes.

ACKNOWLEDGMENT OF GOVERNMENT SUPPORT

This invention was made with government support under contract no. NNX13CC77P awarded by NASA. The government has certain rights in this invention.

BACKGROUND/SUMMARY

Many medical procedures require the removal of bodily fluids such as: saliva and blood during dental procedures, blood and loose tissue during surgery, and vomit, mucous, and saliva during airway management. Bodily fluids may be extracted using a vacuum source, such as a pump, aspirator, etc. A tube or wand coupled to the vacuum source may be directed to the fluid source for collecting the bodily fluids. These fluids may be trapped in a collection vessel so that germs, diseases, and other biological hazards are not transmitted to the environment or vacuum pump. Together, the vacuum source and collection vessel may commonly be referred to as a medical suction device. In some examples, as shown in U.S. Pat. No. 4,930,997, medical suction devices may also include a filter for ensuring that only air passes through the vacuum source to the environment.

However, conventional medical suction devices rely on gravity and buoyant forces to collect liquids in the collection vessel, and seal the collection vessel when it becomes full. As such, traditional collection vessels must be vertically orientated with respect to gravity in order to be properly sealed. In many cases, if the collection vessel is overturned or disoriented, liquids may either prematurely block a safety check valve stopping suction or leak out from the collection vessel, resulting in tedious clean-up procedures and potential disease transmission. Given the nature of emergency responses under a wide variety of field conditions, the probability that the collection vessel is tilted during aspiration is significant. As such, a risk of disease transmission exists with conventional medical suction devices.

In microgravity environments, aspiration poses additional challenges and medical risks. For example, separating liquids from gases and allowing liquid capture within the collection vessel may be difficult. Although centripetal forces may be used to coalesce aspirated liquids and particles from a gas containing stream, trapping the liquids from this stream requires a more complex phase separator that must be incorporated in the collection system.

Another problem with microgravity suction is the manner in which fluids flow to the point of suction from the fluid source. While fluids immediately adjacent to the opening of the tube/wand will be drawn into the tube, contact between the wand and the liquids not immediately adjacent to the wand is maintained only by surface tension forces of the liquids. If the surface tension forces are not sufficient to hold the liquids together, a void may form around the wand during aspiration. As a result, suction may draw only gasses into the device. Thus, in order to collect more liquids from a surface, the vacuum wand must be repositioned on the wetted surface. Because medical suction is often performed on areas with fragile body tissues, scraping a wand, which is typically made of hard plastic, over the relevant surfaces, poses significant risks to a patient.

A substantial amount of air may be drawn into the aspiration system along with liquid and/or solid material when the wand is being repositioned. Further, air may be drawn into the aspiration system during extraction of bodily fluids due to an inability to generate a complete seal between the wand and a complex or fragile surface. Excess gas may prematurely fill the collection vessel, limiting the storage capacity of the vessel, and increasing the risk of leaks.

The inventors herein have recognized the issues described above, and have devised a system for addressing the issues. In particular, a cartridge which may be included in a medical suction device is disclosed herein which comprises a removably coupled bag that may be inserted and removed from the cartridge, for filtering fluids flowing through the cartridge and/or medical suction device.

In one example, a cartridge may include a porous filler material loaded with absorption granules for absorbing liquids, and a hydrophobic liquid barrier which may be permeable only to one or more of air and gasses, and positioned within the cartridge so that fluids in the cartridge may not exit the cartridge without flowing through the barrier. The cartridge may further comprise a disposable bag which is removably coupled to the cartridge, and comprises the porous filler material and the hydrophobic liquid barrier. Additionally or alternatively, the cartridge may comprise a rigid housing, the rigid housing including the porous filler material and the hydrophobic liquid barrier. In some examples, the disposable bag may be included within the rigid housing.

In further examples, the cartridge may include one or more or each of an inlet tube physically coupled to an inlet end of the bag, and an outlet tube. In examples where the bag is flexible, the outlet tube may be physically coupled on one end to an outlet end of rigid housing, and on an opposite end to the vacuum source, so that fluids in the cartridge may flow from the inlet tube, to the disposable bag, and then only gasses may exit the bag to the vacuum source via the outlet tube. However, in examples where the bag is rigid, the outlet tube may be directly physically coupled to the bag. In such examples, the rigid housing may not be included in the cartridge. Thus, the cartridge may comprise only the bag, which may be coupled on one end to the inlet tube, and on the opposite end to the outlet tube. In still further examples of the cartridge, the porous filler material may comprise one or more or each of a reticulated foam with approximately 20 pores per square inch. In other examples of the cartridge, the hydrophobic liquid barrier may comprise porous polytetrafluoroethylenes or other porous hydrophobic membranes.

In other representations, the absorption granules may comprise sodium polyacrylate. A density of the absorption granules in the filler material may increase with increasing radial deflection from a central axis of the bag. In still further examples, the bag may further comprise one or more or each of perforated walls and sealed walls, which may be arranged within the bag in an alternating order and orientated parallel to one another and perpendicular to a flow direction of fluids in the bag, and which may be spaced from one another such that passages are formed between the walls. The perforated walls may be in sealing contact with the bag and may comprise a central opening so that fluids flowing through the bag may flow through the central opening and may not flow around the perforated walls, and where outer edges of the sealed walls may not be in sealing contact with the bag, so that fluids flowing through the bag may flow around and not through the sealed walls. Said another way, a gap may be formed between outer edges along a circumference of the sealed walls and interior surfaces of the bag.

In this way, filtration and removal of liquids and infectious agents from a fluid source may be improved by providing a removably coupled bag in a cartridge with a liquid barrier that prevents liquids from exiting the bag, and traps liquids and potentially infectious agents within the bag. Further, the filtration and absorption efficiency of the cartridge may be maintained despite manipulation of the orientation of the cartridge. Since absorption granules and filler material may be included in the cartridge and may be evenly distributed in the cartridge, absorption and therefore filtration of the bag may be relatively the same regardless of the orientation of the cartridge. Additionally, sanitation levels may be increased and exposure to the liquids may be reduced since the bag may be removably coupled to the cartridge. Thus, the bag may be inserted and attached, or decoupled and removed from the cartridge to provide increased ease of disposal of the liquids.

The above summary is provided to introduce a selection of concepts in a simplified form that are further described below in the Detailed Description. This summary is not intended to identify key features or essential features of the subject matter, nor is it intended to be used to limit the scope of the subject matter. Furthermore, the subject matter is not limited to implementations that solve any or all of the disadvantages noted above or in any part of this disclosure.

BRIEF DESCRIPTION OF THE FIGURES

FIG. 2A shows an external side perspective view of an example cartridge which may be used in a medical suction device such as the medical suction device shown in FIG. 1.

FIG. 2B shows an internal side perspective view of the example cartridge of FIG. 2A.

FIG. 3 shows a cross-sectional view of the example cartridge of FIG. 2A

DETAILED DESCRIPTION

Figure 8:
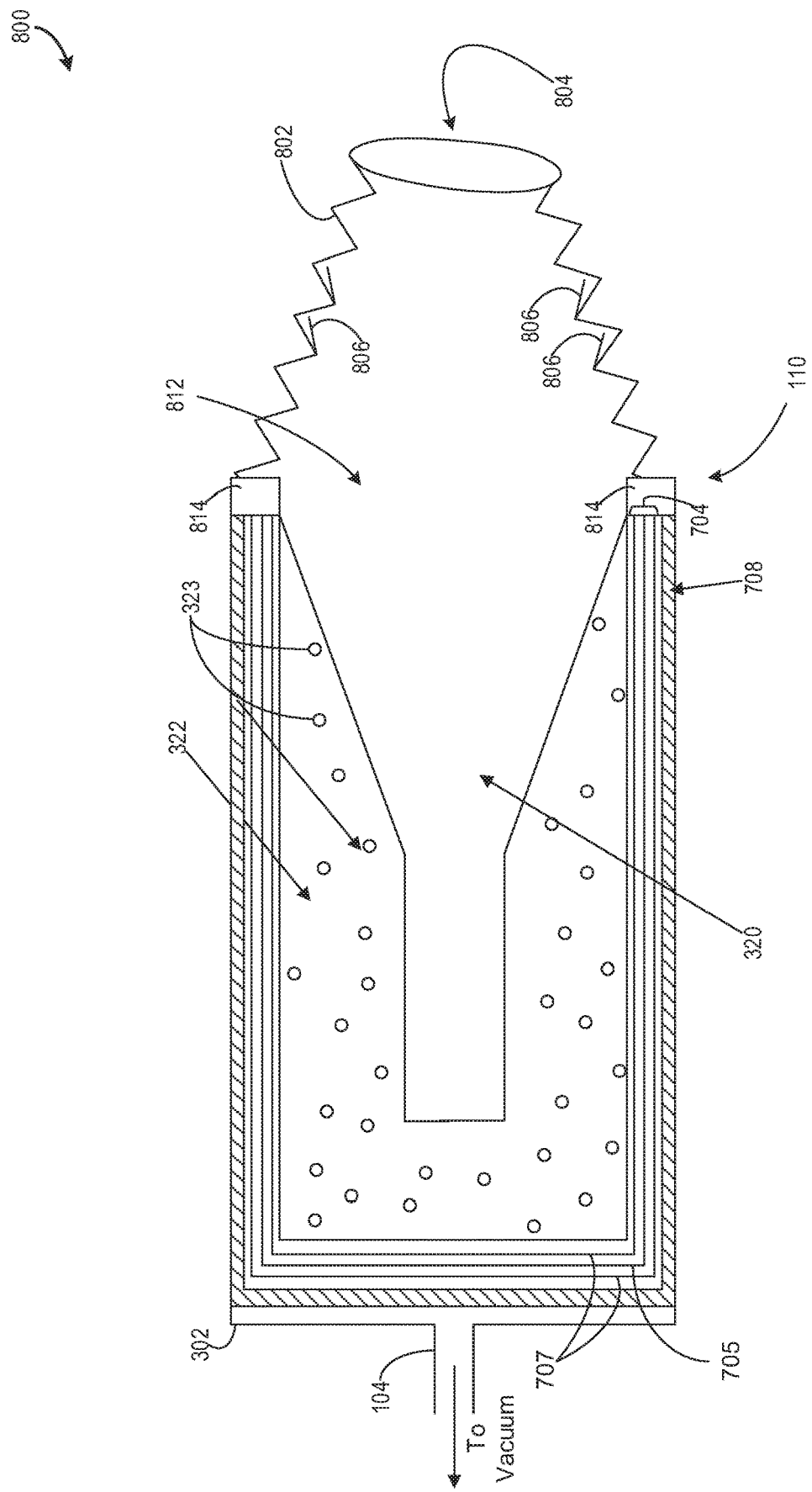
FIG. 8 shows an internal side perspective view of another example cartridge which may be used in a medical suction device such as the medical suction device shown in FIG. 1.

Methods and systems are provided herein for a cartridge which may be used in a medical suction device. Medical suction devices, such as the one shown in FIG. 1, may be used to remove and/or collect bodily fluids from a patient. Fluids may include elements and/or compounds in liquid and/or gaseous form. Thus, fluids may include liquids and/or gasses such as saliva, mucus, blood, water, tears, vomit, and aqueous humor. A vacuum source such as a pump, may be used to provide suction for extracting the bodily fluids. In some examples, a wand/tube of the device may be directed to the fluid source for gathering and collecting the fluids. Fluids entering the device through the wand may then pass into a filtration cartridge (FIGS. 2A-2B) which may comprise a series of alternating flow restriction and expandable hydrophilic layers, as shown in FIGS. 3 and 8. However, in other examples (e.g., FIG. 8), the device may not include a wand, and instead the cartridge may be affixed directly to the fluid source. Example configurations of the flow restriction layers are shown in FIGS. 5A-5D.

Figure 4:
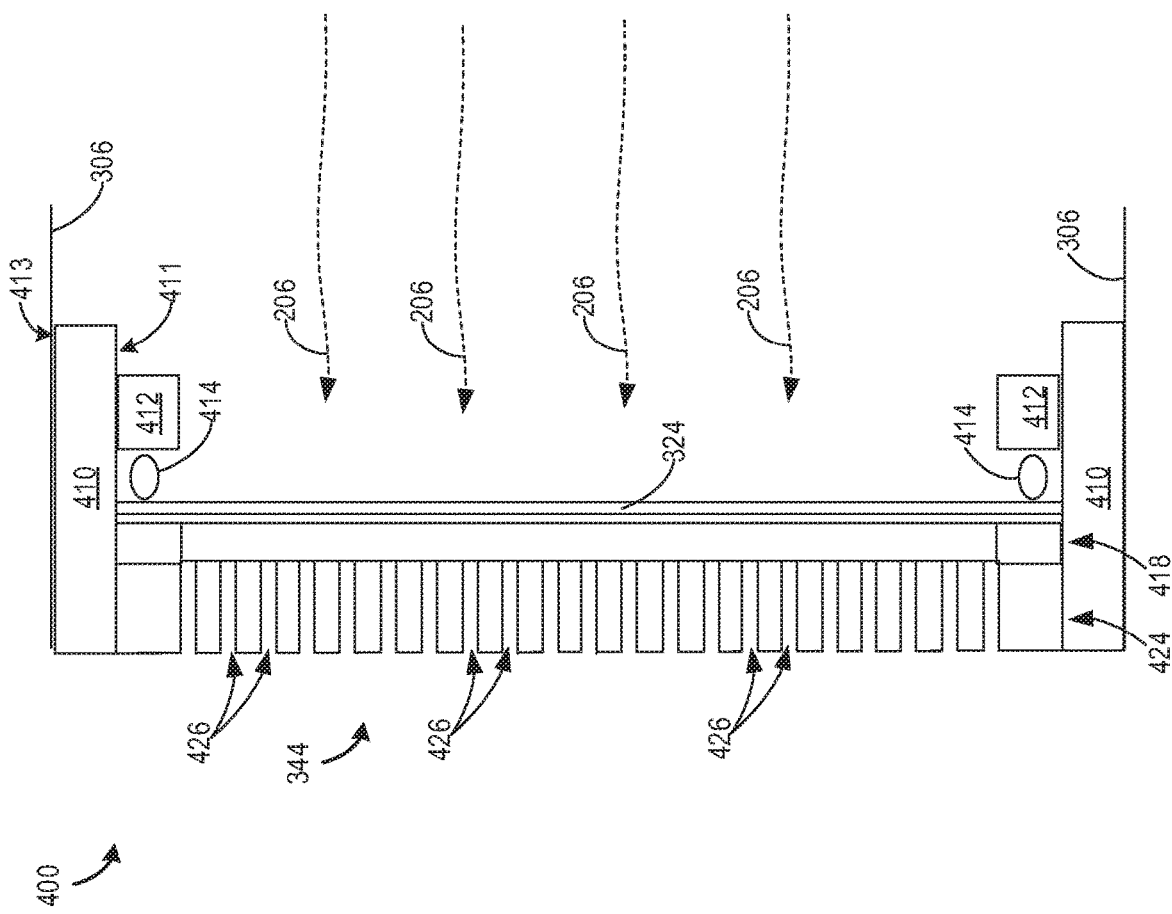
FIG. 4 shows a cross-sectional view of a sealing wall of the example cartridge of FIG. 2A.
Figure 5:
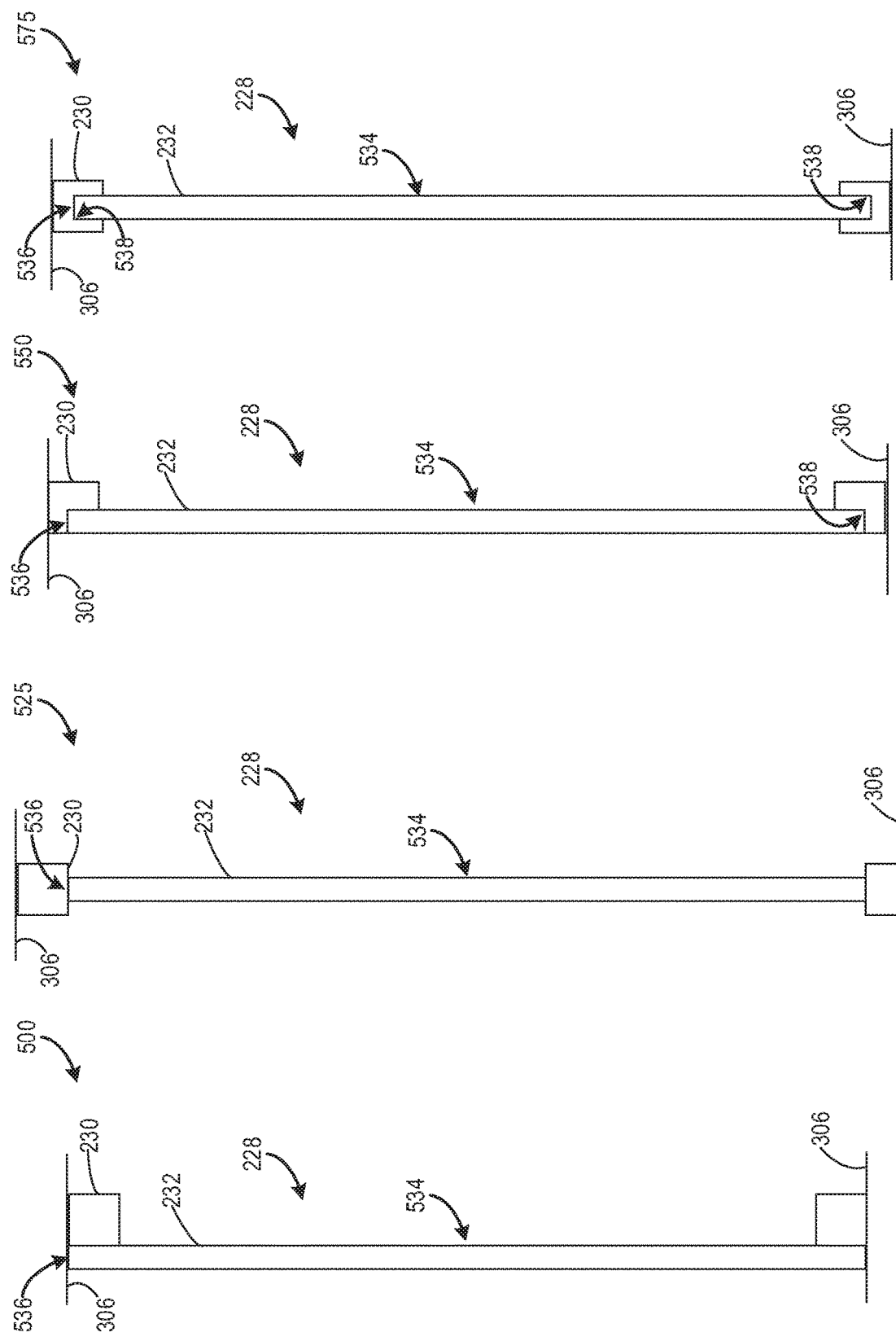
FIG. 5A shows a cross-sectional view of an example configuration of a perforated wall of the example cartridge of FIG. 2A.
FIG. 5B shows a cross-sectional view of an example configuration of a perforated wall of the example cartridge of FIG. 2A.
FIG. 5C shows a cross-sectional view of an example configuration of a perforated wall of the example cartridge of FIG. 2A.
FIG. 5D shows a cross-sectional view of an example configuration of a perforated wall of the example cartridge of FIG. 2A.
Figure 6:
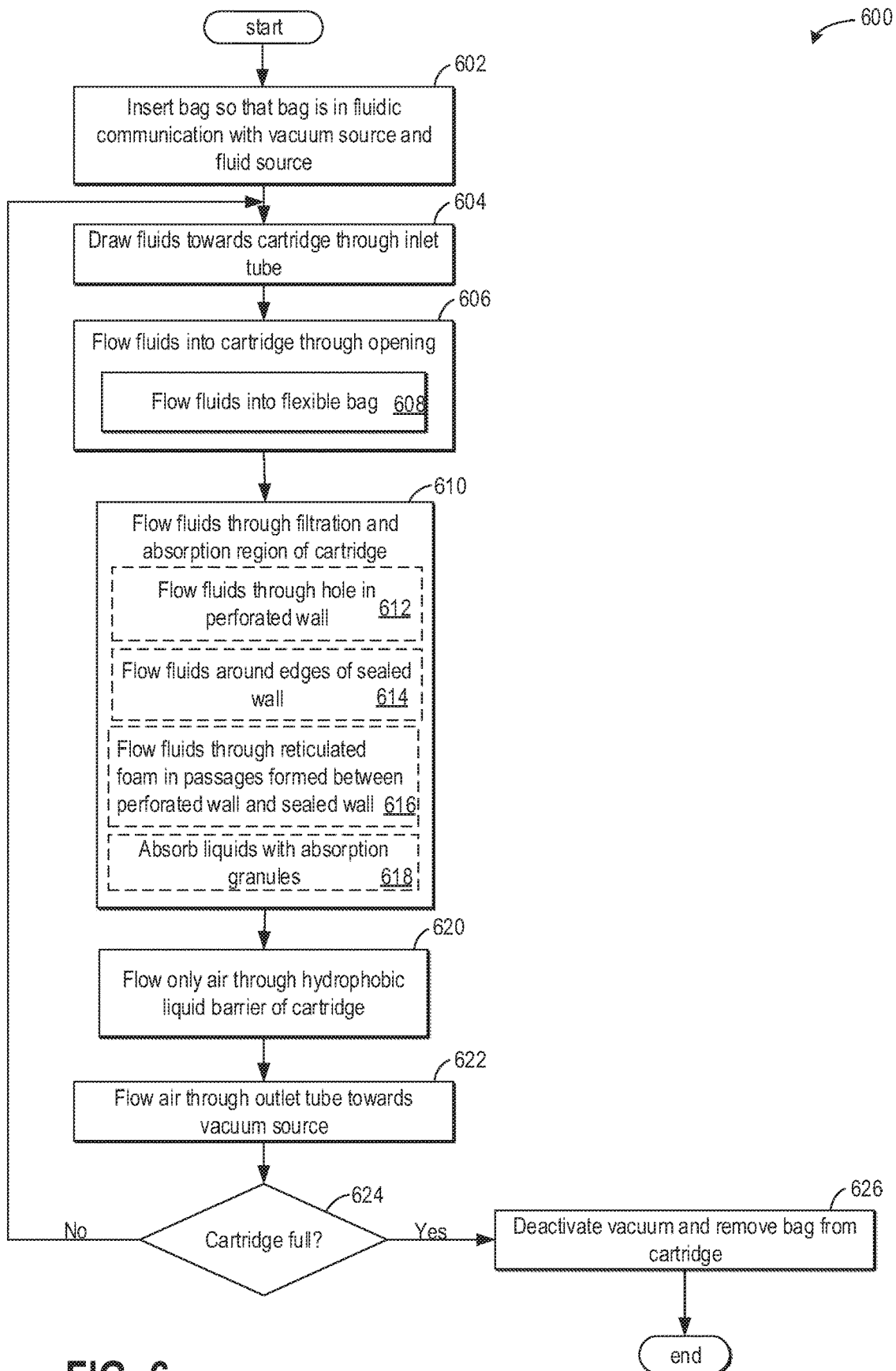
FIG. 6 shows a flow chart of an example method for flowing fluids in a cartridge.

The cartridge may separate gasses from liquids and solids, so that only gasses exit the cartridge to the environment. Gasses may include elements and/or compounds in only their gaseous form, for example, gaseous oxygen, gaseous carbon dioxide, gaseous nitrogen, etc. Solids may include elements and/or compounds in only their solid form. An example method for filtering and absorbing liquids and solids from air in aspirated bodily fluids is shown in FIG. 6. A hydrophobic liquid barrier of the cartridge, as shown in FIG. 4, may ensure that no liquids and/or solids leak through the cartridge. In this way, leakage of fluids and solids to the environment may be reduced, and as such, so too may the risk of disease transmission. Because the device does not rely on gravity for filtration of the bodily fluids, the orientation of the device may not affect its filtration efficiency. Further, since the cartridge is disposable, bodily fluids may be disposed of more efficiently without requiring cleaning of the medical device. As such, the safety, efficiency, and durability of the medical suction device may be increased.

Figure 1:
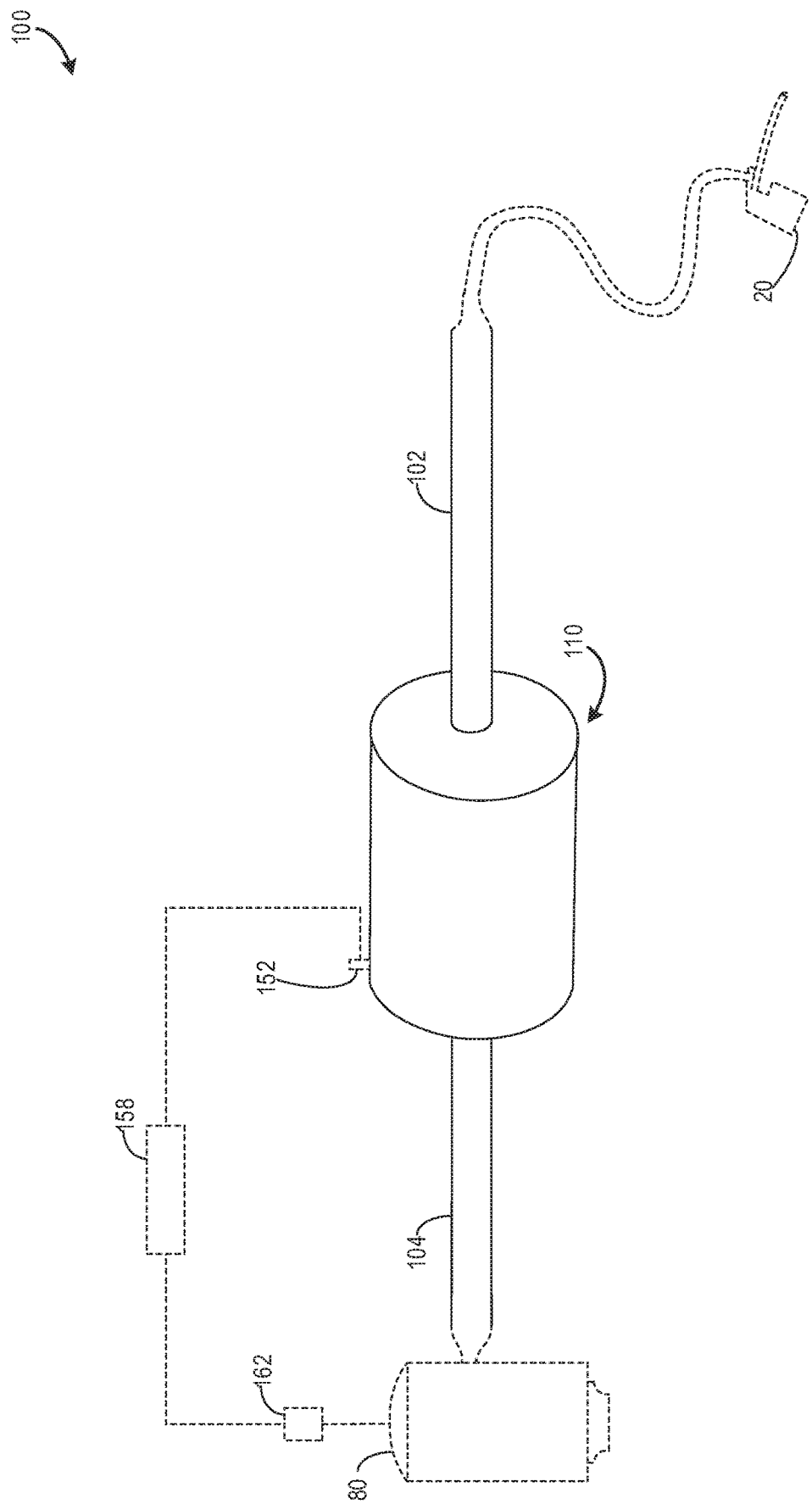
FIG. 1 illustrates a schematic of an example medical suction device.

FIG. 1, shows a schematic of an example of a filtration cartridge 110 which may be used in a medical suction device 100. In some examples, the cartridge 110 may be coupled to a vacuum source 80. A wand 20 may also be fluidically coupled to the cartridge 110 for collecting fluids from a patient. When included, vacuum source 80, may be any suitable device capable of generating suction such as a pump, aspirator, etc. In examples, where the vacuum source 80 is a pump, the pump may be a manual, air driven, or electric pump. Further, the vacuum source 80 may be a rotary vane pump, piston pump, diaphragm pump, etc. Fluids may be collected and drawn into the cartridge by the suction generated from vacuum source 80.

In examples, where wand 20 is coupled to the cartridge 110, inlet tube 102 may be coupled on one end to the filtration cartridge 110, and on the other end to the wand 20. As such, fluids may enter the medical suction device 100 through the wand 20, and may then flow through inlet tube 102 towards the cartridge 110.

However, in examples, where wand 20 is not coupled to the cartridge 110 is therefore not included in the device 100, fluids may enter the medical suction device 100 through inlet tube 102. Thus, in examples where wand 20 is not included in the device 100, inlet tube 102 may be coupled on one end to the filtration cartridge 110 and on the other end may be open to the environment for gathering fluids.

In some further examples inlet tube 102 may not be included in medical suction device 100, and in such examples, filtration cartridge 110 may be exposed directly to the source of fluids for collection thereof. Thus, either the cartridge 110, inlet tube 102, or wand 20 may be in direct physical contact with the surface of a patient, for collecting fluids from the patient. Fluids may enter the medical suction device 100 through an opening in the device due to a suction force generated by the vacuum source 80. Fluids entering the medical suction device 100 flow towards the cartridge 110, where liquids and solids may be filtered out from air and/or other gasses. Thus, as will be explained in greater detail below with reference to FIGS. 2A-8, the filtration cartridge 110 may absorb liquids and/or solids, effectively separating them from gasses in the fluids flowing towards the vacuum source 80. In this way, the filtration cartridge 110 may act as a barrier for liquids and/or solids, preventing them from passing on to the vacuum source 80 and the environment.

Said another way, substantially no liquids and/or solids may flow between the cartridge 110 and the vacuum source 80 along outlet tube 104. Outlet tube 104 may be coupled on one end to the filtration cartridge 110 and on the other end to the vacuum source 80. Thus, only air and/or gasses may flow in outlet tube 104.

Filtration cartridge 110 may be removably coupled to the medical suction device 100. As such the filtration cartridge 110 may be replaced when fluid levels in the cartridge 110 reach a threshold level as explained in greater detail below with reference to FIG. 6. Said another way, the filtration cartridge 110 may be replaced when it becomes full. When inserting a new cartridge 110 into the medical suction device 100, a first end of the cartridge 110 may be physically and/or fluidically coupled to an end of the inlet tube 102, and on the other end to an end of the outlet tube 104. The cartridge 110 may then be removed and physically decoupled from the medical suction device 100 for disposal. In this way, fluids, which may contain potentially infectious agents, may be disposed of with minimal risk of exposure. Therefore, risks of disease transmission, contamination, etc., may be reduced.

In this way, a system for a medical suction device may comprise a vacuum source for generating suction to draw fluids into the device from a fluid source, and a filtration cartridge, for removing liquids and solids from the fluids entering the medical suction device. The filtration cartridge may be configured to absorb and retain liquids and/or solids in the fluids, and may only allow air and/or gasses to pass beyond. Thus, liquids and/or solids in a fluid flow entering the filtration cartridge from a first end, may be trapped inside the cartridge, and may not flow past an opposite second end of the cartridge. A more detailed description of the filtration cartridge is shown below with reference to FIGS. 2A-2B.

Turning now to FIGS. 2A-2B, they show side perspective views of the filtration cartridge 110 shown above in FIG. 1, which may be included in a medical suction device such as medical suction device 100 shown in FIG. 1. As such, components of the medical suction device 100 already introduced in FIG. 1, may not be discussed or reintroduced in the description of FIGS. 2A and 2B. Since, FIGS. 2A and 2B both show side perspective views of the filtration cartridge 110, they will be discussed together in the description herein.

Cartridge 110 may be shaped as a cylinder as shown in the examples of FIGS. 2A and 2B, where walls of the cartridge 110 may be defined by an outer sheath 220 which may house various components of the cartridge 110. Thus, outer sheath 220, may separate interior and exterior portions of the cartridge 110. As such, the cartridge 110 may comprise an inlet end wall 222 and an outlet end wall 224 disposed on either end of side walls 226. The walls 222, 224, and 226 may be physically coupled to one another, so that outer sheath 220 fluidically seals interior and exterior portions of the cartridge, so that fluids may only flow through the cartridge 110 between the inlet tube 102 and outlet tube 104. As described in greater detail in FIG. 3, the outer sheath 220 may comprise one or more of a flexible and disposable bag, and a rigid shell. Wall 222 may include an opening where inlet tube 102 is physically coupled thereto. Further, wall 224 may include an opening where outlet tube 104 is physically coupled thereto. As such, wall 222 and inlet tube 102 may be physically and fluidly sealed, so that fluids flowing in inlet tube 102, may only flow into cartridge 110. Similarly, wall 224 may be physically and fluidly sealed to outlet tube 104, so that fluids flowing through cartridge 110 may only flow out of cartridge 110 through outlet tube 104.

End walls 222 and 224 may be relatively flat and circular. However, in other examples the ends walls 222 and 224 may be shaped differently such as ovular, rectangular, triangular, or other polygonal shapes. In still further examples, the ends walls 222 and 224 may not be shaped as polygons and may take on other geometric or non-geometric shapes. Further, the end walls 222 and 224 may not be flat, and instead may be curved, baffled, undulating, etc. Therefore, the cartridge 110 may take on shapes other than a cylinder. In some examples the cartridge 110 may take on prismatic shapes, such as a rectangular prism, triangular prism, or other polyhedron. In still further examples, the cartridge 110 may take on other three dimensional shapes.

As shown in FIGS. 2A and 2B fluids entering medical suction device 100 may flow through inlet tube 102, towards a vacuum source (e.g., vacuum source 80 shown in FIG. 1). The flow of fluids in the medical suction device 100 is shown by flow arrows 206. Thus, fluids may flow from upstream of the cartridge 110 through inlet tube 102, into the filtration cartridge 110 through inlet end wall 222 of the filtration cartridge 110. After flowing through the filtration cartridge 110, air and/or gasses may flow out of the filtration cartridge 110 through outlet end wall 224 of the filtration cartridge 110, and into the outlet tube 104 downstream of the cartridge 110 towards the vacuum source 80.

Inside filtration cartridge 110, fluids may flow through passages in the cartridge 110, defined by one or more layers. Specifically, flow restriction layers may comprise one or more perforated walls 228 and sealed walls 236, where the perforated walls 228 and sealed walls 236 may be arranged in an alternating fashion. Although FIG. 2A depicts exactly two perforated walls 228 and two sealed walls 236, more or less walls 228 and 236 may be included in the cartridge 110. Thus, in some examples, the number of perforated walls 228 may be greater than two. Similarly, the number of sealed walls 236 may be greater than two. However, the cartridge may include the same number of perforated walls 228 as sealed walls 236. In other examples, the cartridge may include more perforated walls 228 than sealed walls 236. In still further examples, the cartridge may include more sealed walls 236 than perforated walls 228. Additionally, the pattern, arrangement, and spacing of the walls 236 and 228, may be different than depicted in FIG. 2B.

The walls 236 and 228 may be orientated parallel to one another. Further the walls 236 and 228 may be orientated so that they are parallel to walls 222 and 224, and perpendicular to a central axis X-X' of the cartridge 110. As such, the walls 236 and 228 may be positioned perpendicular to the flow of fluids entering the cartridge 110 through inlet tube 102. Further the shape of the walls 236 and 228 may be the same as the end walls 222 and 224. Thus, in examples where the cartridge 110 is cylindrical as is shown in FIGS. 2A and 2B, the walls 236 and 228 may be circular. However, in examples where the cartridge 110 is a rectangular prism, the walls 236 and 238 may be rectangular. Thus, the walls 236 and 228 may be shaped approximately the same as cross-sections of the cartridge 110 parallel to the walls 222 and 224.

As shown in FIG. 2B, the perforated walls 228 may each comprise an opening 234 for providing fluidic communication there-through. Perforated walls 228 may include an inner absorption region 232, and an outer support region 230. The support region 230 may be composed of a rigid material such as acrylic, nylon, plastic ceramic, polymer, etc., while the absorption region 232, may be comprised of a more flexible and/or absorbent material such as felt. However, in other examples, the absorption region 232 may be comprised of a thin non-porous membrane such as a polymer, metal, ceramic, etc. As such, the support region 230 may provide mechanical structure, support and integrity to the absorption region 232, to reduce deformation of the absorption region 232. In some examples, the absorption region 232 may have a width of 2 mm. However, in other examples the absorption region 232 may have a width greater or less than 2 mm. The absorption region may have a width in a range between 0.01 mm and 4 mm.

In some examples, the walls 228 may be sized to have a diameter of approximately 100 mm. However in other examples, the diameter of walls 228 may be greater or smaller than 100 mm. The diameter of walls 228 may be substantially the same as the diameter of the cartridge 110. As such, the edges of the walls 228 may be in face sharing and/or sealing contact with the interior surface of the outer sheath 220. The opening 234 may be formed in the inner absorption region 232. In some examples, the opening 234 may be centrally positioned within each of the perforated walls 228 such that the opening 234 may be centered around a central axis X-X' of the cartridge 110. However, in other examples, the opening 234 may not be centrally positioned on each of the perforated walls 228. In still further examples, the opening 234 may be centrally positioned on one or more of the perforated walls 228, and may not be centrally positioned on one or more of the other perforated walls 228. The opening 234 may be approximately 19 mm in diameter. However, in other examples the opening 234 may be greater than 19 mm in diameter or less than 19 mm in diameter. In some examples, the diameter of the opening 234 may be sized to between ½ an inch and 2 inches. In still further examples, each opening 234 may be sized differently, however, in other examples, each opening 234 may be sized approximately the same. In examples, where the openings 234 are sized differently, the size of the openings 234 may monotonically increase when translating toward wall 224 away from wall 222 along axis X-X.' However, in other examples, the size of the opening 234 may monotonically increase when translating toward wall 222 away from wall 224 along axis X-X.'

Further, in some examples, each of the perforated walls 228 may comprise more than one opening 234. In such examples, all of the perforated walls 228 may comprise more than one opening 234, or only a portion of the perforated walls 228 may comprise more than one opening 234. For each of the perforated walls 228 containing more than one opening 234, the openings may be distributed evenly on the inner absorption region 232. However, in other examples, the openings may be distributed randomly on the region 232. In still further examples, the opening may be distributed on the region 232 according to a mathematical function or distribution, such as Gaussian.

The perforated walls 228 may be physically coupled to the outer sheath 220 of the cartridge 110. Specifically, the outer support region 230 may be physically coupled to the outer sheath 220. As such, the circumference or perimeter of an outer edge of the outer support region 230 may be physically coupled to and fluidically sealed with an interior surface of the outer sheath 220. As such, fluid may only flow through the opening 234 in the perforated walls 228, and may not flow around the perforated walls 228 between the perforated walls 228, and the outer sheath 220.

Conversely, the sealed walls 236, may not comprise an opening 234, and may instead provide a fluidic barrier, whereby fluids may only flow past the sealed walls 236 around edges of the sealed walls 236. As such, the sealed walls 236 may not be coupled to outer sheath 220, so that fluids may flow around the edges of the sealed walls 236, between the edges of the sealed walls 236 and interior surface of the outer sheath 220. Thus, a direction of fluid flow may be reversed as the fluids flow around the edges of the sealed walls 236.

Thus, the sealed walls 236 may comprise a non-porous material such as ceramic, metal, polymer, etc. However in other examples, the sealed walls 236 may comprise a material such as felt that is capable of absorbing some liquids. The walls 236 and 228 may be sized based on their elasticity, so that when more than a threshold differential pressure exists across a wall in the cartridge 110, the wall may deform to allow increased liquid passage to the rest of the cartridge 110. In this way, if the suction pathway becomes blocked, the walls 236 and/or 228 may deform to increase the cross sectional area of the flow path in the cartridge 110, and therefore reduce premature aspiration shut-offs.

Fluids flowing through cartridge 110 may therefore flow around the edges of the sealed wall 236, then through the opening 234 of one of the perforated walls 228 as depicted in FIG. 2A. As described in greater detail below with reference to FIG. 3, after flowing past all of the walls 228 and 236 contained within the cartridge 110, the fluids may reach a hydrophobic liquid barrier as shown in greater detail below in FIGS. 3-4. Cutting plane 240, defines a cross-section of the cartridge 110 shown in FIG. 3

The cartridge of the medical suction device may comprise the disposable bag which may be in sealing contact with the inlet tube, so that fluids flowing through the medical suction device must flow through the disposable bag before flowing to the environment. The disposable bag may be removably coupled to the inlet tube, so that when fluids are not flowing through the medical suction device, the bag may be decoupled and removed from the cartridge for disposal. However, when fluids are flowing through the medical suction device, they may flow through the bag, but only gasses may exit the bag en route to the environment. In some examples, where the bag is configured as a rigid structure, the bag may be removably coupled to both the inlet tube and the outlet tube.

The bag may comprise an absorbent material such as sodium polyacrylate bound to a compressible and expandable filler material positioned between internal walls of the bag. Fluids may be forced to flow through openings and around edges of the walls. As the fluids flow through the bag, the absorbent material may absorb liquids and/or solids. The liquid barrier may be positioned at the end of the bag, so that only gasses may exit the bag. As such, liquids and/or solids may be filtered out from the fluids flowing through the bag, and may be retained within the bag. As the bag becomes filled with liquids and solids, the flow of fluids within the bag may decrease, until fluid flow effectually stops in the bag. At such point, the bag may be removed from the cartridge, and another bag may be inserted into the cartridge.

Turning now to FIG. 3, it shows a cross-sectional view 300 of example cartridge 110 shown in FIGS. 2A-2B, taken along cutting plane 240 shown in FIGS. 2A-2B. As such, components of the cartridge 110 already introduced in FIGS. 2A-2B, may not be discussed or reintroduced in the description of FIG. 3. In FIG. 3, the flow of fluids in the inlet tube 102, outlet tube 104, and cartridge 110 are shown by flow arrows 206. As such, flow through the inlet tube 102, outlet tube 104, and cartridge 110 is generally from right to left in FIG. 3. Said another way, a net flow direction of fluids in the medical suction device 100, is from the inlet tube 102 into the cartridge 110, and out through the outlet tube 104. In the description herein, downstream may be used to refer to components of cartridge 110 positioned downstream (e.g., to the left) relative to other components of the cartridge 110.

Outer sheath 220 (shown in FIGS. 2A and 2B), may comprise one or more of a rigid shell 302, and a disposable bag 306. When included, the rigid shell 302 may be physically coupled to the inlet tube 102, and outlet tube 104, and may not be removable from the tubes 102 and 104. However, in other examples, the rigid shell 302 may be removably coupled to the inlet tube 102 and outlet tube 104, so that the entire cartridge 110, including the rigid shell 302 may be disposed. In some examples where both the rigid shell 302 and bag 306 are included in the cartridge 110, the rigid shell 302 may house the bag 306.

In examples, where both the rigid shell 302 and bag 306 are included in the cartridge 110, the bag 306 may be constructed from a flexible material such as shrink-wrap, plastic film, or moldable polymers. Thus, in examples where the rigid shell 302 is included in the cartridge 110 and the bag 306 is flexible, the bag 306 may be physically coupled only to the inlet tube 102. In other examples, where the bag 306 is flexible, the bag 306 may only be coupled to the rigid shell 302 at end wall 222. As such, the bag 306 may hang inside the rigid shell 302 and may only be physically attached at one or more of the inlet tube 102 and end wall 222. In this way, when vacuum is applied to the cartridge 110, the bag 306 may inflate within the rigid shell 302 due to the differential pressure created across the ends of the cartridge 110 by the vacuum source. In still further examples where the bag 306 is flexible, the bag 306 may be physically coupled to only the outlet tube 104, and not the inlet tube 102.

However, in other examples, the bag 306, may be constructed from a rigid material such as a ceramic, metal, polymer, etc. In such examples, where the bag 306 is rigid, the rigid shell 302 may not be included in the cartridge 110. Further, in examples where the bag 306 is rigid, the bag 306 may be coupled directly to both the inlet tube 102 and the outlet tube 104.

The rigid shell 302 may be sized to fully encompass the bag 306. In some examples the rigid shell 302 may be sized with a diameter of approximately 4 inches. The rigid shell 302, may further be approximately 8 inches long. However, in other examples, the rigid shell 302 may be narrower or wider than 4 inches in diameter, and may be longer or shorter than 8 inches. As such, the rigid shell 302 may also be referred to herein as housing 302. More specifically, a first portion 332 of the rigid shell 302 may be physically coupled to the inlet tube 102, and a second portion 334 of the rigid shell 302 may be physically coupled to the outlet tube 104. Further, the rigid shell 302 may comprise a latch 308, which may fluidically seal the first portion 332 and second portion 334. However, the latch 308 may be adjusted to decouple the first portion 332 and second portion 334 for insertion of bag 306 into the rigid shell 302.

In some examples, as shown in FIG. 3, the inlet tube 102 may extend beyond the rigid shell 302, into the cartridge 110. The rigid shell 302 may be physically coupled to exterior edges 303 of the inlet tube 102 at the end wall 222 of the cartridge 110, so that the inlet tube 102 and rigid shell 302 are in sealing contact with one another. In this way, fluids may only enter the cartridge 110 through the inlet tube 102. Additionally, the rigid shell 302 may be physically coupled to the outlet tube 104 at the end wall 224 of the cartridge 110, so that the outlet tube 104 and rigid shell 302 are in sealing contact with one another. In this way, fluids may only exit the cartridge 110 through the outlet tube 104. The rigid shell 302 may be constructed from a hard plastic such as acrylic. However, in other examples, the rigid shell 302 may be constructed from any non-porous solid such as a polymer, glass, metal, etc.

Additionally, or alternatively, the cartridge 110 may comprise the disposable bag 306 which is removably coupled to the cartridge 110. Thus, the bag 306 may be inserted into and/or removed from the cartridge 110. In some examples, the bag 306 may be inserted into and/or removed from a medical suction device such as the medical suction device 100 shown in FIG. 1. Thus, during insertion of the bag 306 into the cartridge 110, the bag 306 may be coupled to the inlet tube 102.

The disposable bag 306 may be shaped approximately the same as the cartridge 110. Said another way, the disposable bag 306 may define the shape of the cartridge 110 in examples where the rigid housing 302 is not included in the cartridge 110. As such, in examples, where the cartridge 110 is cylindrical as depicted in FIGS. 2A-3, the bag 306 may also be cylindrical. In examples where rigid shell 302 is included in the cartridge 110, the bag 306, may fit inside the rigid shell 302, without deformation of the shape of the bag 306. Said another way, the shell 302 may fully enclose the bag 306. The disposable bag 306 may be made of a flexible shrink wrap film such as poly vinyl chloride (PVC). Further, in some examples, the bag 306 may be made out of any flexible material such as polymeric films or molded polymers such as silicone or acrylic. In still further examples, the bag 306 may be composed of polyolefins. In some examples, the disposable bag 306 may be approximately 0.05 mm thick. However, the thickness of the disposable bag may be a range of thicknesses between 0.005 mm-5 mm.

In some examples, a support lining 304 may be coupled to the bag 306 to increase the strength of the bag 306, and reduce tears or rips in the bag 306 as it expands or stretches due to the different pressure created across the cartridge 110. In some examples, the support lining 304 may be directly physically coupled to the exterior of the bag 306, between the bag 306, and the shell 302. However, in some examples, the support lining 304 may be coupled to the interior of the bag 306.

In particular, the support lining 304 may be physically coupled (e.g., adhered) to the bag 306 via one or more adhesives such as one or more of direct thermal bonding, epoxies, photo curable adhesives, fiberglass resin, thermal adhesive film, etc. The support lining 304 may be adhered to the outside of the bag 306 at one or more of end caps 342 and 344 of the bag 306. In some examples, the support lining 304 may additionally or alternatively be adhered to the outside of the bag 306 at the support region 230 of one or more of the walls 228, where the bag 306 is coupled.

The support lining 304 may comprise a mesh constructed from a clear polymer, such as nylon. The support lining 304 may be substantially optically clear and relatively transparent. The support lining 304 may have a thickness of less than 0.1 inches but more than 0.001 inches. Further, the support lining 304 may have a porosity of between 100 and 10 pores per inch.

In examples where the bag 306 is cylindrical as depicted in FIG. 3, a circumference of the bag 306 may be approximately the same as the circumference of the walls 228 and end caps 342 and 344. Said another way, the bag 306 may be heat shrunk to fit around the edges of walls 228 and end caps 342 and 344. More specifically, the bag 306, may be heat shrunk around a rigid cylindrical shaped tube, which may be sized in diameter approximately the same as the walls 228 and end caps 342 and 344. The bag 306 may comprise one or more of heat shrunk polyvinylchloride, heat shrunk polyethylene, bonded polymer sheeting, and moldable polymers.

In this way the bag 306 may be formed so that the bag 306 may be directly and physically coupled to the edges of walls 228 and end caps 342 and 344, so that the shape of the bag 306 conforms to the shape of the walls 228 and end caps 342 and 344. As such, in some examples, the circumference of the bag may be approximately 13 inches. However, in other examples the circumference of the bag 306 may be greater or less than 13 inches. In still further examples, the circumference of the bag 306 may be a range between 3-30 inches. The disposable bag 306 may be formed as a shrink wrap film, where the shrink wrap film may be composed of any suitable polymer plastic.

Inlet end cap 342 and outlet end cap 344 may be positioned at either end of the disposable bag 306 and physically coupled thereto. Thus, the caps 342 and 344 may form the ends of the bag 306. The caps 342 and 344 may be sized approximately the same as the walls 228. As such, in some examples, the caps 342 and 344 may have a diameter of approximately 100 mm. However, in other examples, the caps 342 and 344 may have a diameter greater than or less than 100 mm. In some examples, the caps 342 and 344 may have a diameter that can range between 1 inch and 10 inches. The inlet end cap 342, may include an opening 346 that may be sized approximately the same as the inlet tube 102, so that the inlet tube 102 may extend through the end cap 342 into the bag 306. In some examples, such as where rigid shell 302 is not included in cartridge 110, the inlet end cap 342 may be fluidically sealed with the edge 303 of the inlet tube 102. The diameter of the inlet tube 102, and therefore the diameter of the opening 346 may be approximately ½ inch. However, the diameter of the inlet tube 102, and opening 346 may be a range between ¼ inch and 3 inches. In other examples, where rigid shell 302 is included in cartridge 110, the end cap 342 may be in sealing contact with the rigid shell 302 via an O-ring 336, positioned between the bag 306 and the rigid shell 302. In this way, bag 306 may be in sealing contact with the inlet tube 102, so that fluids flowing through inlet tube 102 must flow through bag 306 en route to outlet tube 104.

In this way, the bag 306 may be physically coupled to edges of the walls 228, specifically to edges of the support region 230, and to edges of the end caps 342 and 344. Coupling of the bag 306 to the walls 228 and caps 342 and 344 may be achieved using any suitable adhesive such as direct thermal bonding, epoxies, photo curable adhesives, fiberglass resin, thermal adhesive film, etc. In this way, edges of the walls 228 and caps 342 and 344 may be fluidically sealed to interior surfaces of the bag 306, so that fluids may only enter the bag 306 through the opening 346. Further, when flowing through bag 306, fluids may not flow around walls 228 between walls 228 and bag 306, and may only flow through opening 234 in each of the walls 228. However, in other examples, up to a threshold amount of liquids and gasses may flow through the walls 228 and 236. In such examples, however, significantly more liquids flow around the walls 236 than through the walls 236.

Fluids, may therefore flow through inlet tube 102 into the disposable bag 306, through the opening 346 into the bag 306, and enter a hollow collection region 320 of the bag 306. Collection region 320 may be formed between an interior surface 310 of the end cap 342, and one of the perforated walls 228 positioned most proximate the end cap 342 and end wall 222. However, in other examples, the collection region 320 may be formed between an interior surface 310 of the end cap 342, and one of the sealed walls 236 positioned most proximate to the end cap 342 and end wall 222. The collection region 320 may be a hollow portion of the bag, in which increased levels of solid materials may be collected relative to other portions of the bag 306. In some examples, the collection region 320, may only form a small portion of the bag 306. However, in other examples, the collection region may form approximately 50% of the bag 306. The collection region 320 may form a portion of the bag 306 in a range between 0-70 percent of the interior volume of the bag 306.

Thus, after passing through the collection region 320, fluids in the bag 306 may continue through a filtration and absorption region 315 of the bag 306. The filtration and absorption region 315 of the bag 306 may comprise the perforated walls 228 and the sealed walls 236. As shown in the example of FIG. 3, the filtration and absorption region 315 may extend from either a perforated wall 228 or a sealed wall 236 positioned most proximate the end 222 and most distal from the end 224 of the cartridge 110. As such, fluids flowing through the bag 306, may first flow in a first direction through the collection region 320, and then through the opening 234 in one of the perforated walls 228, or around the edges of one of the sealed walls 236. Additionally, solid materials, and more viscous liquids in the fluids may impinge on an upstream surface 329 of one of the perforated walls 228 and/or sealed walls 236. As described above with reference to FIG. 2B, the perforated walls 228 and sealed walls 236 may be arranged parallel to one another, and perpendicular to a net flow direction of fluids in the inlet tube 102, entering the bag 306. As such, the perforated walls 228 and sealed walls 236 may each contain an upstream surface 329 which faces the oncoming flow of fluids in the cartridge 110, and a downstream surface 331, which faces away from the oncoming flow of fluids in the cartridge 110.

Thus fluids may flow through the opening 234 in the perforated walls 228, between the passages 326 formed between the walls 228 and 236, and around the edges of the sealed walls 236, and back towards the opening 234 in the perforated walls 228. In this way, fluid flow may reverse direction as it passes around the edges of the sealed walls 236 as shown by the flow arrows 206 in FIG. 3.

The thickness of the perforated walls 228 and sealed walls 236 may in some examples be approximately the same. However, in other examples the thickness of the walls 228 and 236 may be different. In some examples, the thickness of the walls 228 and 236 may be approximately ¼ inch. However, in other examples, the thickness of the walls 228 may be a range between ¹⁄₃₂ and one inch.

As described above with reference to FIG. 2A, and as depicted in FIG. 3, the perforated walls 228 and sealed walls 236 may be arranged in the bag 306 in an alternating order.

The perforated walls 228 and sealed walls 236 may be spaced from one another such that passages 326 are formed between the perforated walls 228 and sealed walls 236. More specifically, the passages 326 may be formed in the opening 234 of the walls 228, between the upstream surface 329 of each of the sealed walls 236 and the downstream surface 331 of each of the perforated walls, between the upstream surface 329 of each of the perforated walls 228 and the downstream surface 331 of each of the sealed walls, and around the edges of the sealed walls.

The passages 326 may be filled with a porous filler material 322. As such, the filler material 322 may extend between the collection region 320, and a liquid barrier 324 positioned downstream of the filtration and absorption region 315. In some examples, the porous filler material 322 may be rigid. However, in other examples, the porous filler material may be expandable. The porous filler material 322 may include absorption granules 323 which may comprise an absorbent material such as sodium polyacrylate. More specifically, the porous filler material 322 may comprise a polymeric foam substance such as reticulated foam loaded with sodium polyacrylate. The porous filler material 322 may additionally or alternatively be constructed from a rigid, open pore material. In some examples, the porous filler material 322 may include a porosity of approximately 20 pores per square inch. However, in other examples, the filler material 322 may include fewer or more pores per square inch. Sodium polyacrylate, or other absorbent material such as cellulose may comprise the absorption granules 323 and may be adhered to the foam substance to form the filler material 322. Adhesion of the absorption granules 323 to the filler material 322 may be achieved using any suitable adhesive such as epoxy resins, photo curable adhesives, and polyurethane resins.

In other examples, the absorption granules 323 may be cross-linked to other polymers and/or integrally formed in the filler material 322 as a product of co-polymerization. Thus, in some examples, sodium polyacrylate may be integrally formed within the filler material 322.

In some examples, the absorption granules 323 may be distributed evenly on the filler material 322. However, in other examples, the absorption granules 323 may not be distributed evenly on the filler material and may be distributed randomly on the filler material 322. In yet further examples, the absorption granules 323 may be distributed on the filler material 322 according to a mathematical function or distribution such as Gaussian. Specifically, the granules 323 may be distributed on the filler material 322 symmetrically about central axis X-X' and additionally may be distributed such that the concentration of granules 323 increases with increasing deflection away from the central axis X-X' towards the edges of the walls 228 and 236. Put more simply the density of the granules 323 may increase with increasing radial deflection away from the central axis X-X.' Thus, the concentration of granules 323 may be graded radially within the bag 306. Additionally, an amount of absorption granules 323 may increase with increasing deflection towards the end wall 222, away from the end wall 224. In other examples, the relative amount of absorption granules 323 may increase with increasing deflection towards the end wall 224, away from the end wall 222. In this way, absorption of liquids may be greater more proximate the end wall 224 than the end wall 222. Said another way, the hydrophilicity of the filler material 322 may increase with increasing deflection towards the end wall 224, away from end wall 222.

Further, the absorption granules 323 may range in size with diameters between 50-3000 microns. In some examples, the absorption granules 323 may all be the same size. However, in other examples the absorption granules 323 may be differently sized.

Similarly, the porosity of the reticulated foam substance of the filler material 322 may be variable in the filtration and absorption region 315. Specifically, the porosity may, in some examples, increase with increasing deflection towards the end wall 222 away from the end wall 224. However, in other examples, the porosity of the foam substance may increase with increasing deflection away from the end wall 222, towards the end wall 224.

As fluids flow through the passages 326 in the absorption region 315, the liquids may be absorbed by one or more of the absorption granules 323, filler material 322, and walls 228. The absorption granules 323 may expand as they collect liquids and/or solids, and as a result may cause a swelling of the absorption region 315. More specifically, the absorption granules 323 may expand after exposure to liquid, so that their volume increases by a factor of 10-500 with respect to their volume prior to fluid exposure. However, in other examples, the expansion of the absorption granules 323 may be greater or less than 50 times their volume when dry. In this way, the bag 306 may be highly compressible, and as such, may be compressed so that the length of the bag 306 may be variable depending on an amount of liquid stored in the bag 306. Further, the rigid shell 302 may be sized to provide a compressive force on the bag 306 during the absorption of liquids and bag 306 expansion. In this way, the rigid shell 302, may provide mechanical support to the bag 306, and may reduce deformation, and increase the structural integrity of the bag 306.

In this way, disposable bag 306 including porous filler material 322 may be compressible and/or expandable along the direction of axis X-X' shown in FIG. 3. Thus, the filler material 322 may be compressible along the X-X' axis such that the walls 228 and 236 may be displaced along the axis X-X' so that the distance between them, and therefore the width of passages 326 may decrease. As such, when not coupled to the inlet tube 102 and/or outlet tube 104, the bag 306 may be compressed to a smaller first size, and may expand to a larger second size upon coupling of the bag 306 to a vacuum source.

End cap 344 may comprise a hydrophobic liquid barrier 324, such that only air may pass through liquid barrier 324 and end cap 344. In some examples the liquid barrier 324 may be comprised of porous Teflon. However, in other examples, the liquid barrier 324 may be comprised of another material which is permeable to air and/or gasses only such as fluorinated polymers, microporous polypropylenes, polytetrafluoroethylenes, poly sulfone, polyethylene, etc. Thus, as fluids flow through bag 306, upon reaching end cap 344, liquids and/or solids in the fluids may be stopped at the end cap 344, and may not pass beyond end cap 344. Bag 306, may therefore be sealed to liquids and solids at end cap 344. Said another way, liquids and solid upon entering bag 306, liquids and solids may not exit bag 306. A more detailed description of the structure of end cap 344 and liquid barrier 324 is shown below with reference to FIG. 4.

Thus, in some examples, filler material 322 may extend from a downstream surface 331 of the wall 228 positioned most proximate end cap 342 to the end cap 344. As such, the only hollow region in bag 306 may be collection region 320. Further, the filtration and absorptions region may comprise the walls 228 and 236, filler material 322, passages 326, and granules 323. The filtration and absorption region 315 may be positioned immediately downstream and adjacent to the collection region 320, but immediately upstream and adjacent to the liquid barrier 324 and end cap 344.

Flow through the bag 306 may in some examples be passively regulated based on an amount of liquid in the bag 306. Specifically, as liquids are absorbed in the filler material 322 and reach the end cap 344, air flow through the bag 306 may be restricted. Specifically, as liquid is absorbed by the absorption granules 323, the permeability of the filler material 322 may be reduced, and as such airflow through the bag 306 may be reduced. Thus, air flow through the bag 306, may decrease with increasing liquid levels in the bag 306. As such, when liquid levels in the bag 306 reach a threshold, the vacuum level may reach approximately zero. Said another way, fluids, including liquids and gasses, may not be drawn into the cartridge 110, when liquid levels in the cartridge 110 exceed a threshold. Liquids in the cartridge 110 may restrict airflow through the cartridge 110, and therefore an amount of suction drawn from the vacuum source (e.g., vacuum source 80 shown in FIG. 1).

If the amount of liquid in the bag 306 is below the threshold, and air and/or gasses are flowing through the cartridge 110, air and/or gasses may pass through the end cap 344, and into the outlet tube 104. As such, only air and/or gasses may exit the cartridge 110, and air and/or gasses may only exit the cartridge through the outlet tube 104.

However, in other examples, the flow through the bag 306 may be actively regulated based on outputs from a sensor 152. In some examples, sensor 152 may be an electronic vacuum gauge or differential pressure sensor, and thus outputs from the sensor 152 may be used to estimate a pressure drop across the bag 306. In such examples, the sensor 152 may be included between the cartridge 110 and the vacuum source. As the bag 306 fills with liquid, the air passages in the bag 306 may become blocked and as a result the vacuum between the cartridge 110 and the vacuum source may increase. In response to the pressure differential across the cartridge 110 increasing above a threshold, the bag 306 may be decoupled and removed from the inlet tube 102 and cartridge 110. In some examples, the threshold pressure differential may represent a pressure differential level across the bag 306 at which substantially no fluids flow through the cartridge 110.

In still further examples, the sensor 152 may be configured as a mass airflow sensor, and outputs from the sensor 152 may be used to estimate an airflow through the bag 306. In such examples, the sensor 152 may be coupled between the cartridge 110 and the vacuum pump for estimating airflow from the cartridge 110 to the vacuum source. Air flow may decrease as fluid levels in the bag 306 increase, since the fluids may increase restriction to flow within the bag 306. In response to the airflow through the cartridge 110 decreasing below a threshold, the bag 306 may be decoupled and removed from the inlet tube 102 and cartridge 110. In some examples, the threshold airflow may represent an airflow rate through the cartridge 110 at which fluids are no longer flowing through the cartridge 110.

As described above, when the pressure differential across the cartridge 110 and/or air flow through the cartridge reach respective thresholds, the bag 306 may be decoupled and removed from inlet tube 102 and cartridge 110. Specifically, in examples where the rigid shell 302 is included in the cartridge 110, the latch 308 may be adjusted so that the two portions 332 and 334 of the rigid shell 302 may be decoupled from one another for removal of the bag 306. The bag 306 may then be physically decoupled from the inlet tube 102. In examples where the bag 306 is rigid and rigid shell 302 is not included in the cartridge 110, the bag 306 may be physically decoupled from both the inlet tube 102 and the outlet tube 104. Upon removal of the bag 306, another bag 306 may be inserted into the cartridge 110, and the two portions 332 and 334 of the rigid shell may be fit around the bag 306, and coupled together via the latch 308. The latch 308 may provide a vacuum seal around the bag 306.

In this way, a cartridge may comprise a disposable bag which is removably coupled to a medical suction device, for filtering fluids suctioned from a patient. The disposable bag may be configured to absorb liquids and/or solids in the fluids, and prevent liquids and/or solids from passing through the bag to the environment. When liquids and/or solid levels in the bag reach a threshold, signaling that the bag is full, fluid flow in the bag may be terminated, and subsequently the bag may be removed for disposal thereof. Another bag may be inserted into the cartridge for continued filtration of the fluids. A more detailed description of the shutoff mechanism which terminates the fluid flow in the bag, is shown below with reference to FIG. 4.

Turning now to FIG. 4, it shows a cross-sectional view 400 of end cap 344 shown above in FIG. 3, taken along cutting plane 240 shown in FIGS. 2A-2B. Components of end cap 344 already described above in FIG. 3 may be similarly numbered in FIG. 4, and may not be reintroduced or discussed in the description of FIG. 4 herein. As described above with reference to FIG. 3, end cap 344 may restrict the flow of liquids and/or solids from the bag 306 to the outlet tube 104. Said another way, the end cap 344, may confine liquids and/or solids to within the bag 306. Specifically, the hydrophobic liquid barrier 324 may be impenetrable to liquids and/or solids. As described above, the liquid barrier 324 may be made of porous polytetrafluoroethylene (PTFE) or more commonly referred to as Teflon. However, in other examples, the liquid barrier 324 may be constructed from materials other than Teflon that are impermeable to liquids and solids, but are permeable to air and/or gasses. In some examples, the liquid barrier 324 may contain pore sizes of approximately 0.45 microns. However, in other examples, the liquid barrier 324 may contain pores ranging in size from 0.02 to 8 microns.

The end cap 344 may further comprise an end plate 424 which may be made from plastic. The end plate 424 may include narrow channels 426, which may allow for air to pass through the end plate 424. The end plate may be sized to a width of approximately 6 mm. However, in other examples the width of the end plate 424 may be greater or less than 6 mm. In still further examples, the width of the end plate 424 may range between 1 and 40 mm. Further, the channels 426 may range in size between 0.01-3 mm.

An intermediate filter 418 may be positioned between the end plate 424 and the liquid barrier 324. The intermediate filter 418 may comprise fritted glass, and may be configured to direct gasses having passed through the liquid barrier 324 to the channels 426 in the end plate 424. Thus, the end plate 424 is positioned downstream of the liquid barrier 324 relative to the flow of fluids in the bag 306. Said another way, the end plate 424 is positioned more proximate the outlet tube 104 shown in FIGS. 2A-3 than the liquid barrier 324. As such, fluids flowing through the bag 306, contact the liquid barrier 324 before reaching the end plate 424.

Additionally or alternatively, a sealing ring 414 may be positioned between the liquid barrier 324 and a retaining ring 412, for providing a fluidic seal between the liquid barrier 324, bag 306, and retaining ring 412. The retaining ring 412 may be physically coupled to support plate 410. The sealing ring 414 may be in sealing contact with the support plate 410, and liquid barrier 324, thereby ensuring that fluids flowing in the bag 306 may flow only through liquid barrier 324, and not around liquid barrier 324.

In an alternate embodiment, sealing ring 414 and retaining ring 412 may not be included in end cap 344, and the liquid barrier 324 may be directly physically coupled to support plate 410 to ensure that fluids may flow only through the liquid barrier 324 and not around the liquid barrier 324. In one example, edges of the liquid barrier 324 may be glued around the perimeter of the liquid barrier 324 to interior surfaces of the support plate 410. In other examples, the perimeter of the liquid barrier 324 may be heat or melt sealed to the interior surface of the support plate 410.

One or more of end plate 424, intermediate filter 418, liquid barrier 324, sealing ring 414, and retaining ring 412 may be physically coupled to support plate 410. Support plate 410 may also be physically coupled to bag 306. Thus, support plate 410 may be coupled on an interior facing surface 411 to one or more of end plate 424, intermediate filter 418, liquid barrier 324, retaining ring 412, and sealing ring 414, and on an opposite externally facing surface 413 to the bag 306. In this way, end cap 344 may be integrally formed into the bag 306. Support plate 410 may be physically coupled to bag 306 using any suitable adhesive and/or thermal adhesive.

In this way, the liquid barrier 324 may ensure that only gasses and/or air may pass through the end cap 344. The liquid barrier 324 may be in physical and sealing contact with the bag 306, via support plate 410, retaining ring 412, and sealing ring 414, so that fluids must pass through the liquid barrier 324 en route to the outlet tube 104 shown in FIGS. 1-3. As such, fluids may not flow out of bag 306 without first flowing through liquid barrier 324.

Moving on to FIGS. 5A-5D, they show different embodiments of structural configurations of the walls 228 shown in FIGS. 2-3. As such, FIGS. 5A-5D may be discussed together in the description herein. Components of walls 228 already introduced in FIGS. 2-3 may not be reintroduced or discussed further in the description of FIGS. 5A-5D herein. The walls 228 shown in FIGS. 5A-5D are cross sectional views of the walls 228 taken along cutting plane 240 shown above in FIGS. 2A-2B.

As described above with reference to FIGS. 2B-C, the support region 230 of the walls 228 may be physically coupled to the absorption region 232 of the walls 228. The support region 230 may be physically coupled to the bag 306 shown in FIG. 3. In some examples, as shown in the embodiment 500 of FIG. 5A, the support region 230, may be physically coupled to a side surface 534 of the absorption region 232. More specifically, the support region 230 may be coupled to the absorption region 232, so that the support region 230 is flush with respect to edges 536 of the absorption region 232. In such examples, both edges 536 of the absorption region 232, and the support region 230 may physically contact the bag 306 shown in FIG. 3. Further, the support region 230 and/or the absorption region 232 may be physically coupled to the bag 306.

However, in other embodiments, as shown in the embodiment 525 of FIG. 5B, the support region 230 may be physically coupled to the absorption region 232 at the edges 536 of the absorption region 232, and not at a side surface 534. In such examples, the support region 230 may be positioned between the absorption region 232 and the bag 306 shown in FIG. 3.

In still further examples, as shown in the embodiment 550 of FIG. 5C, the support region 230 may be physically coupled to both a side surface 534 and edges 536 of the absorption region 232. Thus in some examples, the support region 230, may include an inset mount 538, where the support region 230 may physically contact the absorption region 232 at more than one surface. In another example, as shown in the embodiment of FIG. 5D, the support region 230 may be physically coupled to more than one side surface 534, and edges 536 of the absorption region 232. Thus, the support region 230, may comprise more than one inset mount 538, so that the support region 230 extends around the edges 536 of the absorption region 232.

In this way, the bag 306 may expand or contract in a lateral direction while retaining its structural integrity. Specifically, the lateral direction of movement may be such that the walls 228 move closer to one another, or move away from one another, but remain parallel to one another. Thus, as shown in FIG. 3, end caps 344 and 342 may move towards one another when the bag 306 contracts in the lateral direction, and may move away from one another when the bag 306 expands in the lateral direction while maintaining approximately parallel positioning. Said another way, the upstream and downstream surfaces 329 and 331 respectively, may remain approximately perpendicular to one another during expansion and/or contraction of the bag 306.

Turning now to FIG. 6, it shows a flow chart of an example method 600 for flowing fluids through a medical suction device (e.g., medical suction device 100 shown in FIGS. 1-2B). In particular, method 600 shows a means for absorbing liquids, and filtering liquids and solids from gasses in a fluid stream in a cartridge which may comprise a portion of a medical suction device.

Method 600 begins at 602 by inserting a bag (e.g., disposable bag 306 shown in FIGS. 3-5D) so that the bag is in fluidic communication with a vacuum source (e.g., vacuum source 80 shown in FIG. 1) and a fluid source (e.g., wand 20 shown in FIG. 1). Specifically, inserting the bag may comprise receiving the bag in a cartridge (e.g., cartridge 110 shown in FIGS. 1-3). As such, the method 600 at 602 may in some examples, comprise receiving the bag in a rigid shell (e.g., rigid shell 302 shown in FIG. 3) of the cartridge. Further, the method 600 at 602 may comprise physically coupling a first end (e.g., end cap 342 shown in FIG. 3) of the bag to an inlet tube (e.g., inlet tube 102 shown in FIGS. 1-3). In examples where the rigid shell is not included in the cartridge and therefore the bag is rigid, the method 600 at 602 may additionally comprise physically coupling an opposite second end (e.g., end cap 344 shown in FIG. 3) of the bag to an outlet tube (E.g., outlet tube 104 shown in FIGS. 1-3) so that the bag is in sealing contact with both the inlet tube and the outlet tube. However, in examples where the rigid shell is included in the cartridge, the method at 602 may comprise only physically coupling the bag to the inlet tube and not to the outlet tube. In this way, the method 600 at 602 may comprise ensuring that any fluids flowing through the medical suction device must flow through the bag.

After the bag is received in the cartridge at 602, method 600 continues to 604 which comprises drawing fluids towards the cartridge through the inlet tube. Thus, the method 600 at 604 may include applying a vacuum source (e.g., vacuum source 80 shown in FIG. 1) to a fluid source for drawing fluids towards the vacuum source. The cartridge may be positioned between the vacuum source and the fluid source, as shown above with reference to FIG. 1, so that the vacuum source may draw fluids towards the cartridge. In this way, the method 600 at 604 may comprise generating vacuum from a vacuum source, and applying the generated vacuum or suction to a source of fluids, and drawing in the fluids from the inlet tube towards the cartridge.

Method 600 may then proceed to flow the fluids drawn in through the inlet tube, into the cartridge through an opening in the cartridge at 606. However, in examples, where the inlet tube is not included in the medical suction device, and the cartridge is coupled directly to the source of fluids, the method 600 may not execute 604, and may proceed directly from 602 to 606. As such, the method 600 may in some examples comprise flowing fluids into the cartridge without flowing the fluids through the inlet tube. More specifically, the method 600 at 606 may further comprise at 608, flowing the fluids through an opening (e.g., opening 346 shown in FIG. 3) in the bag, which may be in sealing contact with exterior surfaces (e.g., exterior edges 303 shown in FIG. 3) of the inlet tube. In examples where the cartridge includes the rigid shell, the method 600 at 606 may additionally comprise flowing the fluids through the inlet tube, and into the rigid shell before flowing the fluids into the bag. As described above with reference to FIG. 3, the inlet tube may extend into the rigid shell, and/or may be integrally formed as part of the rigid shell. Thus, the method 600 at 606 may comprise directing fluids into the bag through the opening in the bag, and not around the bag. In this way, fluids flowing through the inlet tube, flow towards the cartridge, and into the bag.

Once fluids have entered the bag at 606, method 600 may then proceed to 610, which comprises flowing fluids through a filtration and absorption region (e.g., filtration and absorption region 315 shown in FIG. 3) of the cartridge. As described above in FIG. 3, the filtration and absorption region may comprise perforated walls (e.g., perforated walls 228 shown in FIGS. 2B-3, and 5), sealed walls (e.g., sealed walls 236 shown in FIGS. 2B-3), and reticulated foam (e.g., filler material 322 shown in FIG. 3) loaded with absorbent granules (e.g., absorption granules 323 shown in FIG. 3). Specifically, the absorbent granules may comprise sodium polyacrylate. However, in other examples, the absorbent granules may comprise other absorbent material such as cellulose.

As such, the method 600 at 610 may additionally comprise one or more of flowing fluids through a hole (e.g., opening 234 shown in FIGS. 2B-3) in the perforated walls at 612, flowing fluids around edges of the sealed walls at 614, flowing fluids through the reticulated foam in passages (e.g., passages 326 shown in FIG. 3) formed between the perforated walls and sealed walls at 616, and absorbing liquids from the fluids in the absorption granules at 618. Specifically, the method 600 at 610 may comprise flowing fluids through the hole which may be centrally positioned in the perforated walls, and into a passage formed between the perforated wall and a sealed wall positioned adjacent and downstream to the perforated wall. Next, fluids may be directed through the reticulated foam which occupies the passage formed between the perforated wall and sealed wall, away from the center of the sealed wall, towards the edges of the sealed wall between an upstream surface (e.g., upstream surface 329 shown in FIG. 3) of the sealed wall and a downstream surface (e.g., downstream surface 331 shown in FIG. 3) of the perforated wall. The fluids may be then be flowed around the edges of the sealed wall, and back towards the center of the sealed wall, on the opposite downstream surface of the sealed wall between the downstream surface of the sealed wall, and an upstream surface of a perforated wall positioned downstream and adjacent to the sealed wall. Upon reaching the opening of the downstream perforated wall, the fluids may be flowed through the opening of perforated wall and into the passage formed between the perforated wall and a sealed wall position adjacent and downstream to the perforated wall.

The method 600 at 610 may comprise repeating 612, 614, 616, and 618, until the fluids are flowed through the entire filtration and absorption region of the cartridge. Thus, the method 600 may comprise flowing fluids through the holes in all of the perforated walls, and around the edges of all of the sealed walls of the cartridge. However, in other examples, the method 600 at 610 may comprise only flowing fluids through a portion of the filtration and absorption region, and not flowing fluids past all of the perforated walls and/or sealed walls. In still further examples, the method 600 at 610 may comprise flowing air and/or gasses through the entire filtration and absorption region of the cartridge, but flowing liquids and/or solids through only a portion of the filtration and absorption region of the cartridge. Thus, in such examples, the method 600 at 610 may comprise flowing air and/or gasses through all of the holes in the perforated walls, around the edges of all of the sealed walls, and through all of the passages formed between the perforated walls and the sealed walls in the cartridge. However, the method 600 at 610 may additionally or alternatively comprise flowing liquids and/or solids only through a portion of the holes in the perforated walls, and only flowing the fluids around the edges of a portion of the sealed walls, and only through a portion of the passages formed between the perforated walls and the sealed walls.

Method 600 may proceed from 610 to 620 and flow only air and/or gasses through a hydrophobic liquid barrier (e.g., liquid barrier 324 shown in FIGS. 3-4) positioned downstream of the filtration and absorption region. As such, the method 600 at 620 may additionally comprise restricting the flow of liquids and/or solids, so that effectively no liquids and/or solids flow past the liquid barrier. In this way, the method 600 at 620 may comprise impeding the flow of liquids and/or solids in the bag, so that no liquids and/or solids flow out of the bag. Said another way, the flow of liquids and/or solids may be effectively stopped at the liquid barrier at 620.

After flowing only air through the liquid barrier at 620, method 600 may continue to 622 which comprises flowing air through the outlet tube towards the vacuum source. Thus, air may exit the bag through the liquid barrier, and then continue towards the vacuum source through the outlet tube. However, in some examples where the bag is coupled directly to the vacuum source and/or the outlet tube is not included in the medical suction device, the method 600 at 620 may comprise flowing air to the vacuum source from the bag, not through the outlet tube.

Method 600 may then proceed from 622 to 624 which comprises determining if the cartridge is full. Determining if the cartridge is full may comprise determining if the fluid level in the bag is greater than a threshold. The threshold may represent a fluid level, above which, may restrict airflow through the bag, so that the total airflow through the bag may be approximately zero. As explained above with reference to FIG. 3, in examples, where fluid flow through the bag is passively controlled, determining if the cartridge is full may be based on airflow through the bag. In other examples, determining if the cartridge is full may be based on a pressure differential across the cartridge. Thus, when airflow through the bag reduces to below a threshold airflow and/or a pressure differential increases above a threshold pressure drop, it may be determined that the cartridge is full.

In some examples, the threshold may represent approximately zero airflow through the bag. However, in other examples, the airflow may be greater than zero.

In examples, where fluid flow through the bag is actively controlled, the determining if the cartridge is full may be based on outputs from a one or more of a differential pressure sensor and/or a mass airflow sensor (e.g., sensor 152 shown in FIG. 3). Specifically a controller (e.g., controller 158 shown in FIG. 1) may receive signal outputs from the sensor, and may determine based on the outputs if the fluid level is above a threshold. Specifically, fluid levels may be inferred based on one or more of the differential pressure across the cartridge, and/or a mass airflow rate through the cartridge. As described above with reference to FIG. 3, the differential pressure across the cartridge may increase for increases in fluid levels in the cartridge. Further mass airflow rates through the cartridge may decrease for increases in the fluid level in the cartridge. In this way, if one or more of the differential pressure increases above a threshold pressure differential, and/or the mass airflow rate decrease below a threshold mass airflow rate, then the controller may infer that the fluid level in the cartridge is above the threshold. If the controller determines that the fluid level is above the threshold, then the controller may determine that the cartridge is full. However if the controller determines that the one or more of the pressure differential across the cartridge is less than the threshold pressure differential and/or the airflow through the cartridge is greater than the threshold mass airflow rate, then the controller may determine that the cartridge is not full.

If it is determined at 624 that the cartridge is full, then method 600 may continue to 626 and deactivate the vacuum and/or remove the bag from the cartridge. The removal of the bag from the medical suction device may comprise decoupling the bag from the inlet tube and outlet tube, so that the bag is no longer in fluidic communication with the inlet tube and outlet tube. In examples, where the rigid shell is included in the medical suction device, the rigid shell may be opened by adjusting a latch (e.g., latch 308 shown in FIG. 3) of the rigid shell, to separate two portion (e.g., portions 332 and 334 shown in FIG. 3) of the rigid shell. Opening the rigid shell by adjusting the latch, may decouple the two portions of the rigid shell, thereby exposing the bag. After opening the rigid shell, the bag may be removed from the medical suction device by decoupling it from the inlet tube. Thus, in examples where the rigid shell is included in the medical suction device, the bag may only be physically coupled to the inlet tube, and not to the outlet tube.

In examples where the sensor is not included in the medical suction device, and fluid flow through the cartridge is passively controlled, the reducing and/or deactivating of the vacuum at 626 may include restricting and/or filling air passages in the bag via absorption of liquids. Thus, as liquids are absorbed by the absorption granules such as at 618, the passages in the bag may become impermeable to airflow, and as such airflow through the bag may be reduced. As such, the method 600 at 626 may include absorbing liquids with the absorption granules, until airflow through the bag is effectively zero, and the vacuum drawn from the medical suction device is deactivated. Additionally or alternatively, the vacuum source may be turned off by an operator of the medical suction device.

However, in examples, where the sensor is included in the medical suction device, and fluid flow through the cartridge is actively controlled, the controller may send signals to an actuator (e.g., actuator 162 shown in FIG. 1) physically coupled to the vacuum source for decreasing power supplied to the vacuum source, to decrease an amount of vacuum generated by the vacuum source. In examples where the pump is a rotary vane pump, the method 600 at 626 may comprise reducing the speed at which the actuator rotates blades of the pump, to reduce the vacuum generated by the pump. In some examples, the reducing the power supplied to the vacuum source may comprise reducing power to zero and turning off the vacuum source. Method 600 may then return from 626.

However, if at 624 it is determined that the bag and/or cartridge is not full, then method 600 may return to 604 and continue to flow fluids through the bag and/or cartridge. Thus, the method 600 may comprise flowing fluids through the bag and/or cartridge until the bag is full of liquids and solids. Said another way, the method 600 may comprise flowing fluids through the bag until liquid levels in the bag reach a threshold level, so that airflow through the bag decreases below a threshold.

Figure 7:
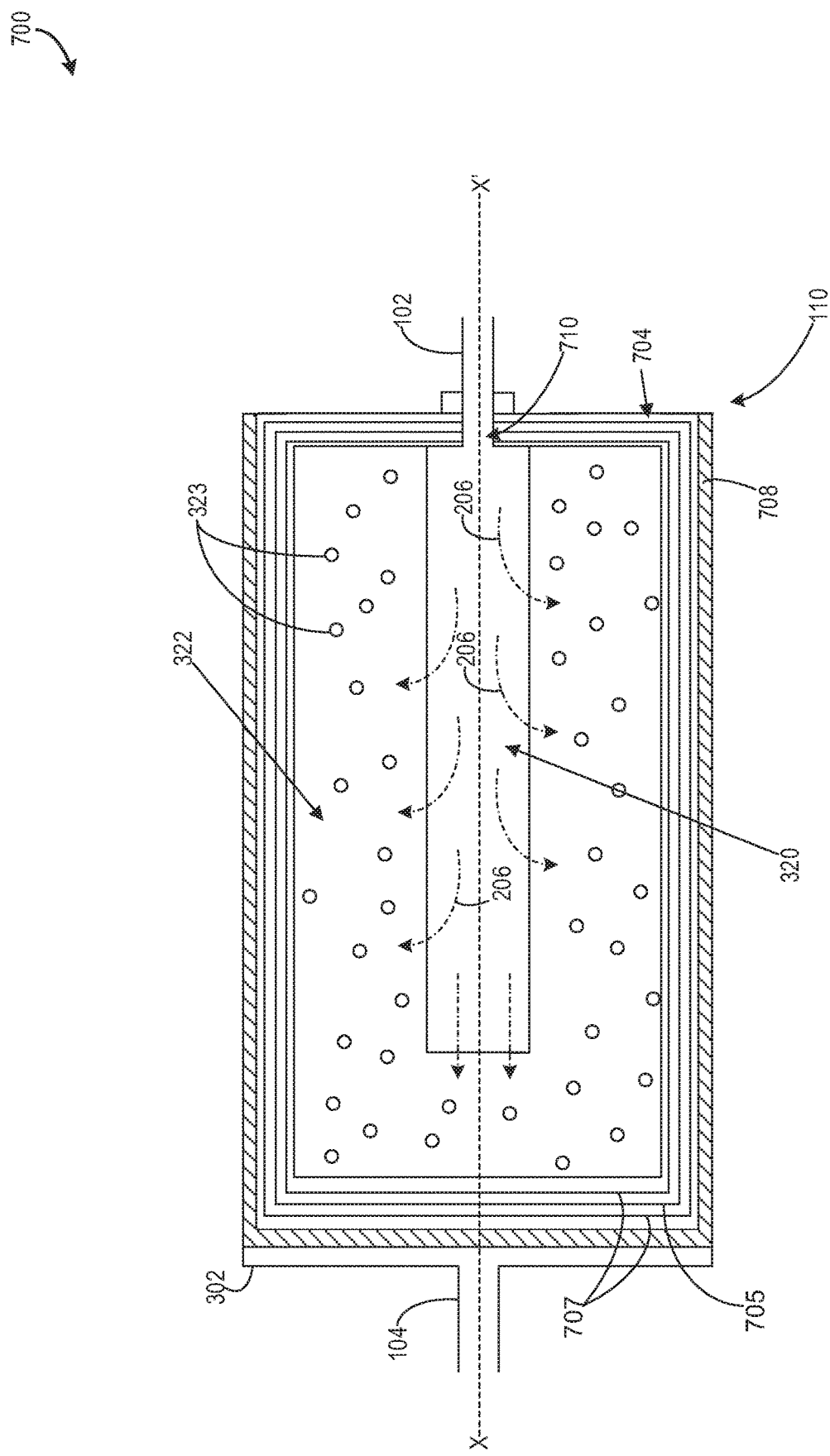
FIG. 7 shows an internal side perspective view of another example cartridge which may be used in a medical suction device such as the medical suction device shown in FIG. 1.

Turning now to FIG. 7, it shows a cross-sectional view of an alternate embodiment 700 of example cartridge 110 shown in FIGS. 2A-2B, taken along cutting plane 240 shown in FIGS. 2A-2B. As such, components of the cartridge 110 already introduced in FIGS. 2A-5, may not be discussed or reintroduced in the description of FIG. 7.

In the embodiment 700 of cartridge 110, cartridge 110 may not include the perforated walls 228 and sealed walls 236 shown in FIG. 3. Instead a hydrophobic liquid barrier 704 may be contained within the rigid shell 302, and may encompass the filler material 322 with the absorption granules 323. As such, the filler material 322 may occupy the entire volume defined by the liquid barrier 704, except for the collection region 320. The collection region 320 may extend from an opening 710 in the liquid barrier 704, into the interior of the liquid barrier, and may be centered around the central axis X-X' of the cartridge 110.

The opening 710 of the liquid barrier 704 may be sized so that the liquid barrier 704 is physically and fluidically coupled to the inlet tube 102. Thus, the liquid barrier 704 and inlet tube 102 may be in sealing contact with one another, so that fluids flowing through the inlet tube 102, may only flow into the interior of the liquid barrier 704, specifically into the collection region 320. Further, the inlet tube may extend through the rigid shell 302, through the liquid barrier 704, and into the collection region 320. As such no fluids flowing through the inlet tube 102 may flow through the cartridge 110 without first flowing through the collection region 320 and filler material 322. Upon entering the collection region 320, fluids may then flow both radially and longitudinally along axis X-X' away from the point of entry through opening 710. As such, fluids flow through the filler material 322 and absorption granules 323 contained therein. After flowing through the filler material 322, only air and/or gasses may flow through the liquid barrier 704. The liquid barrier 704 may be similar in composition to the liquid barrier 324 described above with reference to FIG. 3, and as such may be comprised of Teflon.

Further, the liquid barrier 704 may comprise three distinct layers: a center or middle layer 705, and two bordering layers 707. The center layer 705 may be constructed from a thin porous Teflon membrane. The other two bordering layers 707 may be porous but may provide support and protection to the Teflon membrane from physical damage. In some examples, the liquid barrier 704 may comprise more or less than three layers. Each of the layers may be the same width, however in other examples the layers may be different widths. The width of the liquid barrier 704 may be approximately 4 mm. However the width of the liquid barrier may be a range of widths between 1 mm and 10 mm.

Air passages 708 may be formed between exterior edges of the liquid barrier 704 and the rigid shell 302. After flowing through the liquid barrier 704, air and/or gasses only may flow through the air passages 708, around the liquid barrier 704, to the outlet tube 104, en route to the vacuum source. However, in other examples, as described below in FIG. 8 the inlet tube 102 may not be included and the cartridge 110 may be directly coupled to a fluid source.

Turning now to FIG. 8, it shows a cross-sectional view of an alternate embodiment 800 of example cartridge 110 shown in FIG. 7. As such, components of the cartridge 110 already introduced in FIGS. 2A-7 may not be discussed or reintroduced in the description of FIG. 8. The embodiment 800 of cartridge 110 is different from the embodiment 700 of cartridge 110 described in FIG. 7, in that the cartridge 110 in the embodiment 800 may not include inlet tube 102 shown in FIGS. 1-5, and 7.

In the embodiment 800 of cartridge 110, cartridge 110 may not include the perforated walls 228 and sealed walls 236 shown in FIG. 3 as described above in FIG. 7. Instead the hydrophobic liquid barrier 704 may be contained within the rigid shell 302, and may encompass the filler material 322 with the absorption granules 323. Additionally, the cartridge 110 may not include inlet tube 102 shown in FIGS. 1-5, and 7. Instead, the cartridge 110 may be coupled to a compressible hose 802 which may be in direct contact with fluids, for collection thereof.

The compressible hose 802 may be physically coupled to a sealing ring 814. Thus the sealing ring 814 may be physically coupled on one end to the hose 802, and on the other end to one or more of the rigid shell 302, liquid barrier 704, and filler material 322. As such the sealing ring 814 may provide a fluidic seal between the cartridge 110 and the hose 802. Specifically, the sealing ring 814 may provide a fluidic seal between the rigid shell 302, liquid barrier 704, and the hose 802. In this way, fluids flowing through the hose 802, flow to the collection region 320, and then to the liquid barrier 704. Fluids flowing through the hose 802 may not flow through air passages 708 without first flowing through filler material 322 and liquid barrier 704.

The hose 802 may comprise a flexible plastic material such as PVC, and as such the hose 802 may be extended or compressed depending on the distance between the cartridge 110 and the fluid source. Fluids may be sucked through an opening 804 in the hose 802, and carried towards the cartridge 110. The hose 802 may further include check vents 806, for reducing backflow of fluids in the hose 802. Check vents 806 may allow for bidirectional airflow there-through. Thus, the check vents 806 may allow for a patient to wear the suction device over their mouth and continue to breathe while wearing the suction device.

The opening 812 may extend within the interior of the sealing ring 814. As such fluids entering the cartridge may flow through the opening 812, between interior edges of the sealing ring 814, and into the collection region 320 of the cartridge 110. Solids and/or liquids may be collected in the collection region 320. The diameter of the collection region 320 may increase with increasing proximity to the opening 812, as shown in the example in FIG. 8. Thus, the collection region 320 may form a fan-shaped hollow interior of the cartridge 110. Near the opening 812, the collection region 320 may extend across the diameter of the barrier 704. As described above with reference to FIG. 7, fluids may flow into the collection region 320 and through the filler material 322. Liquids may be absorbed by the absorbent granules, and the liquid barrier 704 may prevent liquids and/or solids from escaping to the air passages 708, so that only air and/or gasses may pass through to the air passages 708 en route to the outlet tube 104, and vacuum source.

In this way, a medical suction device may comprise a vacuum source which may be operable to generate vacuum and provide suction for fluids. As such, fluids may be drawn into the medical suction device by the vacuum generated by the vacuum source. The vacuum source may be coupled to a filtration cartridge, so that fluids flowing through the medical suction device may be forced through the filtration cartridge. The filtration cartridge comprises a disposable bag, which may be removably coupled to the medical suction device. In some examples, a rigid shell may encapsulate the bag, and provide mechanical support for the bag. The rigid shell may be opened via adjusting of a latch, so that the bag may be easily removed and inserted into the cartridge.

A reticulated foam filler material may be included within the bag, which may be sufficiently porous to allow gasses and/or liquids to pass there-through. Additionally, absorbent granules which may comprise sodium polyacrylate may be physically coupled to the filler material, so that liquids may be absorbed by the filler material. Absorbing of the liquids by the granules may result in a swelling and/or expansion of the filler material and therefore the bag. As described above, the rigid shell may provide a compressive force on the bag, so that deformation of the bag may be reduced during absorption of liquids and/or solids.

Further, the bag may comprise a hydrophobic liquid barrier, which may prevent liquids and/or solids from passing there-through. After passing through the filler material, fluids may contact the liquid barrier, and only air and/or gasses may flow through the barrier. As such, the flow of liquids and/or solids in the cartridge may stop at the liquid barrier. In this way, liquids and/or solids may enter but not exit the cartridge. Further, substantially all liquids and/or solids flowing into the cartridge may be trapped within the bag.

In some examples, fluids may enter the cartridge through an inlet tube, physically coupled to the rigid shell and/or bag. Specifically, the rigid shell and inlet tube may be integrally formed as a part of the medical suction device. The inlet tube may extend into the rigid shell, and may be physically coupled to the bag. Specifically, the bag and inlet tube may be in sealing contact with one another, so that substantially all of the fluids flowing through the inlet tube into the cartridge flow into the bag, and not around the bag. In some examples, an end of the bag may be in sealing contact with the rigid shell and inlet tube via a sealing ring positioned between the bag and the rigid shell (Only if the bag has a rigid surface).

In still further examples, the bag may comprise a series of perforated and sealed walls. The perforated walls may comprise a central hole, allowing for fluid flow there-through. The perforated walls may further be coupled to and in sealing contact with the bag, so that fluid may not flow around the perforated walls. However, the sealed walls may only allow fluid to flow around their edges. All of the walls may be positioned parallel to one another and perpendicular to the direction of flow of fluids entering the cartridge. As such, fluids may flow through filler material positioned in passages formed between upstream and downstream surfaces of the perforated walls and sealed walls.

However, in other examples, the medical suction device may not contain an inlet tube, and instead may comprise a hose which may be coupled to the cartridge on one end, and extended to reach a fluid source on the other end. In such examples, fluids may enter the medical suction device through an opening in the hose, and may be directed to the cartridge through the hose. After flowing through the liquid barrier, and/or gasses may pass onto one or more of an outlet tube and/or the vacuum source.

In one representation, a cartridge for a medical suction device comprises a porous filler material loaded with absorption granules for absorbing liquids, a hydrophobic liquid barrier, permeable only to one or more of air and gasses, and positioned within the cartridge so that liquids in the cartridge cannot exit the cartridge, and a disposable bag removably coupled to the cartridge, the bag including the porous filler material and the hydrophobic liquid barrier. In a first example of the cartridge, the porous filler material is expandable. A second example of the cartridge optionally includes the first example and may further comprise, a rigid housing, the rigid housing including the disposable bag. A third example of the cartridge optionally includes one or more of the first and second examples, and may further comprise an inlet tube physically coupled to an inlet end of the bag and an inlet end of the rigid housing, and an outlet tube physically coupled on one end to an outlet end of the rigid housing and on an opposite end to the vacuum source, such that fluids flow into the bag via the inlet tube, and then only gasses exit the bag and flow to the vacuum source via the outlet tube. A fourth example of the cartridge optionally includes one or more of the first through third examples, and may further include wherein the hydrophobic liquid barrier is positioned at an outlet end of the bag, the outlet end opposite the inlet end of the bag. A fifth example of the cartridge optionally includes one or more of the first through fourth examples, and may further include wherein the hydrophobic liquid barrier comprises one or more of polytetrafluoroethylenes, fluorinated polymers, poly sulfone, polyethylene, and polypropylene. A sixth example of the cartridge optionally includes one or more of the first through fifth examples, and may further include wherein the disposable bag comprises one or more of heat shrunk polyvinylchloride, heat shrunk polyethylene, bonded polymer sheeting, and moldable polymers. A seventh example of the cartridge optionally includes one or more of the first through sixth examples, and may further include wherein the absorption granules comprise sodium polyacrylate or cellulose. An eighth example of the cartridge optionally includes one or more of the first through seventh examples, and may further comprise, perforated walls and sealed walls, arranged within the bag in an alternating order and orientated parallel to one another and perpendicular to a net flow direction of fluids in the bag, and spaced from one another such that passages containing the porous filler material are formed between the walls. A ninth example of the cartridge optionally includes one or more of the first through eighth examples, and may further include wherein the perforated walls are in sealing contact with the bag and comprise a central opening such that fluids flowing through the bag flow through the central opening and not around the perforated walls, and where the sealed walls are not in sealing contact with the bag, such that fluids flowing through the bag flow around and not through the sealed walls. A tenth example of the cartridge optionally includes one or more of the first through ninth examples, and may further comprise, a compressible hose physically coupled to an inlet end of the bag, where the hose further contains an opening for collecting fluids, and directing them towards the bag.

In another representation, a method may comprise flowing fluids in a first direction into a cartridge via an inlet tube coupled to the cartridge, directing fluids through passages formed in the cartridge between walls positioned perpendicular to the first direction of fluid flow, where the passages include a porous filler material loaded with absorption granules, and absorbing liquids from the fluids with the absorption granules. In a first example of the method, the method may further comprise inserting a bag into the cartridge prior to flowing the fluids into the cartridge, and fluidically sealing the bag at only an inlet end to the inlet tube so that fluids flowing into the cartridge flow through the bag and not around the bag. A second example of the method optionally includes the first example and may further comprise, generating a vacuum and coupling the vacuum to the cartridge for flowing fluids through the cartridge from the inlet tube. A third example of the method optionally includes one or more of the first and second examples and may further include, where the directing the fluids through the passages further comprises, flowing fluids through a central opening in a perforated wall, and around edges of a sealed wall, where a direction of fluid flow is reversed around the edges of the sealed wall. A fourth example of the method optionally includes one or more of the first through third examples and may further include deactivating the vacuum in response to an airflow through the cartridge decreasing below a threshold, and removing the bag from the cartridge. A fifth example of the method optionally includes one or more of the first through fourth examples and may further include wherein removing the bag from the cartridge comprises opening a rigid shell which houses the bag, and physically decoupling the bag from the cartridge, so that the bag is not in sealing contact with the inlet tube.

In another representation, a medical suction device comprises a cartridge including a porous filler material loaded with absorption granules for absorbing liquids and a hydrophobic liquid barrier for preventing liquids from passing through the cartridge, an inlet tube coupled to a first end of the cartridge, the inlet tube including an opening for collecting fluids from a fluid source and delivering them to the cartridge, and a vacuum source coupled to a second end of the cartridge, the second end opposite the first end, for flowing fluids through the inlet tube to the cartridge. In a first example of the medical suction device, the medical suction device may further comprise where the inlet tube comprises a compressible hose, the compressible hose including check vents that provide bidirectional airflow there-through. In a second example of medical suction device, the medical suction device may optionally include the first example, and may further comprise, a three layer membrane encompassing the porous filler material, where a middle layer of the three layer membrane is composed of porous polytetrafluoroethylene (PTFE).

In this way a technical effect of increasing filtration and removal of liquids and infectious agents from a fluid source is achieved by providing a cartridge with a liquid barrier that prevents liquids from exiting the cartridge, and traps liquids and potentially infectious agents within the cartridge. Further, by including absorbent granules in expandable filler material of the cartridge that absorb and remove liquid from a fluid flow in the cartridge, filtration of the fluid flow may be improved. Further, another technical effect of maintaining the filtration and absorption efficiency of the cartridge despite manipulation of the orientation of the cartridge is achieved by the cartridge with the absorption granules and liquid barrier. Since the absorption granules and filler material may be relatively evenly distributed in the cartridge, absorption and therefore filtration of the cartridge may be relatively the same regardless of the orientation of the cartridge.

Another technical effect of increasing sanitation levels of the medical suction device is achieved by providing a removably coupled bag, which may be inserted and attached, or decoupled and removed from a medical suction device to provide increased disposal efficiency. Thus, the removably coupled bag may be inserted and fluidically sealed within the cartridge to filter fluids flowing in the cartridge during aspiration of fluids. When the bag is full, the bag may be removed and disposed of, so that contact with liquids and/or solids in the fluids and the bag may be reduced, and therefore potential transmission of diseases and/or infectious agents may be reduced.

Another technical effect of increasing filtration efficiency in microgravity environments is achieved by a bag with absorption granules and filler material. Since the bag requires only a vacuum source to draw fluids through the cartridge, the filtration efficiency of the bag is relatively unaffected by forces of gravity. The filtration of fluids in the bag may therefore be determined by the absorption capability of the bag, and may not be influenced by gravitational forces.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

Note that the example control and estimation routines included herein can be used with various medical suction device configurations. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium, where the described actions are carried out by executing the instructions in a system including the various engine hardware components in combination with an electronic controller.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A cartridge for a medical suction device comprising:
a porous filler material loaded with absorption granules for absorbing liquids;
a hydrophobic liquid barrier, permeable only to one or more of air and gasses, and positioned within the cartridge preventing liquids from exiting the cartridge;
a disposable bag removably coupled to the cartridge, the bag including the porous filler material and the hydrophobic liquid barrier, and perforated walls and sealed walls, arranged within the bag in an alternating order and orientated parallel to one another and perpendicular to a net flow direction of fluids in the bag, and spaced from one another such that passages containing the porous filler material are formed between the walls.

2. The cartridge of claim 1, wherein the porous filler material is expandable.

3. The cartridge of claim 1, further comprising a rigid housing, the rigid housing including the disposable bag.

4. The cartridge of claim 3, further comprising an inlet tube physically coupled to an inlet end of the bag and an inlet end of the rigid housing, and an outlet tube physically coupled on one end to an outlet end of the rigid housing and on an opposite end to a vacuum source, such that fluids flow into the bag via the inlet tube, and then only gasses exit the bag and flow to the vacuum source via the outlet tube.

5. The cartridge of claim 4, wherein the hydrophobic liquid barrier is positioned at an outlet end of the bag, the outlet end opposite the inlet end of the bag.

6. The cartridge of claim 1, wherein the hydrophobic liquid barrier comprises one or more of polytetrafluoroethylenes, fluorinated polymers, poly sulfone, polyethylene, and polypropylene.

7. The cartridge of claim 1, wherein the disposable bag comprises one or more of heat shrunk polyvinylchloride, heat shrunk polyethylene, bonded polymer sheeting, and moldable polymers.

8. The cartridge of claim 1, wherein the absorption granules comprise sodium polyacrylate or cellulose.

9. The cartridge of claim 1, wherein the perforated walls are in sealing contact with the bag and comprise a central opening such that fluids flowing through the bag flow through the central opening and not around the perforated walls, and where the sealed walls are not in sealing contact with the bag, such that fluids flowing through the bag flow around and not through the sealed walls.

10. The cartridge of claim 1, further comprising a compressible hose physically coupled to an inlet end of the bag, where the hose further contains an opening for collecting fluids, and directing them towards the bag.

11. A method comprising:
flowing fluids in a first direction into a cartridge via an inlet tube coupled to the cartridge;
directing fluids through passages formed in the cartridge between walls positioned perpendicular to the first direction of fluid flow, where the passages include a porous filler material loaded with absorption granules; and
absorbing liquids from the fluids with the absorption granules.

12. The method of claim 11, further comprising inserting a bag into the cartridge prior to flowing the fluids into the cartridge, and fluidically sealing the bag at only an inlet end to the inlet tube so that fluids flowing into the cartridge flow through the bag and not around the bag.

13. The method of claim 11, further comprising generating a vacuum and coupling the vacuum to the cartridge for flowing fluids through the cartridge from the inlet tube.

14. The method of claim 11, where the directing the fluids through the passages further comprises, flowing fluids through a central opening in a perforated wall, and around edges of a sealed wall, where a direction of fluid flow is reversed around the edges of the sealed wall.

15. The method of claim 12, further comprising deactivating the vacuum in response to an airflow through the cartridge decreasing below a threshold, and removing the bag from the cartridge.

16. The method of claim 15, wherein removing the bag from the cartridge comprises opening a rigid shell which houses the bag, and physically decoupling the bag from the cartridge, so that the bag is not in sealing contact with the inlet tube.

17. A medical suction device comprising:
a cartridge including a porous filler material loaded with absorption granules for absorbing liquids and a hydrophobic liquid barrier for preventing liquids from passing through the cartridge;
an inlet tube coupled to a first end of the cartridge, the inlet tube including an opening for collecting fluids from a fluid source and delivering them to the cartridge;
a vacuum source coupled to a second end of the cartridge, the second end opposite the first end, for flowing fluids through the inlet tube to the cartridge; and
a three layer membrane encompassing the porous filler material, where a middle layer of the three layer membrane is composed of polytetrafluoroethylene (PTFE).

18. The medical suction device of claim 17, where the inlet tube comprises a compressible hose, the compressible hose including check vents that provide bidirectional airflow there-through.

* * * * *